United States Patent
Oka et al.

(10) Patent No.: US 9,466,146 B2
(45) Date of Patent: Oct. 11, 2016

(54) IMAGE PROCESSING APPARATUS, IMAGE PROCESSING METHOD AND DATA STRUCTURE OF IMAGE FILE

(71) Applicants: Sony Corporation, Tokyo (JP); Sony Computer Entertainment Inc., Tokyo (JP)

(72) Inventors: Masaaki Oka, Kanagawa (JP); Satoru Seko, Kanagawa (JP); Yoshiki Okamoto, Kanagawa (JP); Masaaki Hara, Tokyo (JP)

(73) Assignees: Sony Corporation, Tokyo (JP); Sony Interactive Entertainment Inc., Tokyo (JP)

( * ) Notice: Subject to any disclaimer, the term of this patent is extended or adjusted under 35 U.S.C. 154(b) by 0 days.

(21) Appl. No.: 14/356,753

(22) PCT Filed: Oct. 23, 2012

(86) PCT No.: PCT/JP2012/006767
§ 371 (c)(1),
(2) Date: May 7, 2014

(87) PCT Pub. No.: WO2013/069215
PCT Pub. Date: May 16, 2013

(65) Prior Publication Data
US 2014/0306952 A1    Oct. 16, 2014

(30) Foreign Application Priority Data
Nov. 10, 2011    (JP) .................... 2011-246279

(51) Int. Cl.
*G06T 15/00*    (2011.01)
*G06T 15/10*    (2011.01)
(Continued)

(52) U.S. Cl.
CPC ............ *G06T 15/10* (2013.01); *A61B 5/00* (2013.01); *G06T 11/20* (2013.01); *G06T 15/08* (2013.01);
(Continued)

(58) Field of Classification Search
CPC ........ G06T 11/20; G06T 15/08; G06T 15/10; A61B 2576/00; A61B 5/05; A61B 5/015; A61B 5/1032; A61B 5/00; A61B 5/0073; A61B 2562/043
USPC ........................................................ 345/419
See application file for complete search history.

(56) References Cited

U.S. PATENT DOCUMENTS

2002/0110274 A1* 8/2002 Yamamoto ............ G06T 11/40
                                                    382/154
2003/0128242 A1* 7/2003 Gordon ..................... 345/848
(Continued)

FOREIGN PATENT DOCUMENTS

EP    1001376 A2    5/2000
EP    1416443 A2    5/2004
(Continued)

OTHER PUBLICATIONS

JP 2003-263651 (machine translation on Jul. 8, 2015).*
(Continued)

*Primary Examiner* — Phi Hoang
*Assistant Examiner* — Michael Le
(74) *Attorney, Agent, or Firm* — Matthew B. Dernier

(57)    ABSTRACT

In an image processing apparatus, a sensor output data acquisition unit acquires data of layered image information from a sensor group. A slice image generation unit generates data of a two-dimensional image for each slice plane surfaces in which distribution is acquired. An image axis conversion unit generates similar data of a two-dimensional image for a plurality of plane surfaces that are perpendicular to an axis different from a sensor axis. A slice image management unit of a display processing unit manages a slice image that is used for drawing according to the position of a viewpoint or the like. Memory for drawing sequentially stores data of an image necessary for drawing. An additional object image storage unit stores image data of an object that is additionally displayed such as a cursor or the like. An image drawing unit draws a three-dimensional object using data of the slice image.

13 Claims, 18 Drawing Sheets

(51) Int. Cl.
G06T 15/08 (2011.01)
A61B 5/00 (2006.01)
G06T 11/20 (2006.01)
A61B 5/01 (2006.01)
A61B 5/05 (2006.01)
A61B 5/103 (2006.01)

(52) U.S. Cl.
CPC .............. A61B 5/0073 (2013.01); A61B 5/015 (2013.01); A61B 5/05 (2013.01); A61B 5/1032 (2013.01); A61B 2562/043 (2013.01); A61B 2576/00 (2013.01)

(56) References Cited

U.S. PATENT DOCUMENTS

| 2005/0231503 | A1 | 10/2005 | Heng | |
|---|---|---|---|---|
| 2007/0206008 | A1* | 9/2007 | Kaufman et al. | 345/424 |
| 2009/0135180 | A1* | 5/2009 | Li | 345/420 |
| 2009/0195552 | A1* | 8/2009 | Nystad | G06T 11/40 345/611 |
| 2011/0069070 | A1* | 3/2011 | Engel | 345/426 |

FOREIGN PATENT DOCUMENTS

| JP | 5-266215 A | 10/1993 |
|---|---|---|
| JP | 2003-263651 A | 9/2003 |
| JP | 2005011043 A | 1/2005 |
| WO | 0163561 A1 | 8/2001 |

OTHER PUBLICATIONS

JP 05-266215 (machine translation on Jul. 8, 2015).*
International Search Report for the corresponding PCT Application No. PCT/JP2012/006767, dated Nov. 20, 2012.
International Preliminary Examination Report on Patentability (I) with Written Opinion for the corresponding PCT Application No. PCT/JP2012/006767, dated May 13, 2014.
Koichi Matsuda et al., "Interactive Arbitrary 6 Cross-Section Visualization Using 2D-Texture on Standard PC", The Transactions of the Institute of Electronics, Information and Communication Engineers(J85-D-II), Aug. 1, 2002, No. 8, pp. 1351 to 1354 (for relevancy see IPRP for PCT/JP2012/006767 dated May 13, 2014.
Office Action for corresponding JP Application No. 2011-246279, 3 pages, dated Aug. 18, 2015.
European Search Report for corresponding EP Application No. 12847428.5, 11 pages, dated Dec. 4, 2015.
Orion Wilsont Allen Van Celder, Jane Wilhelms: "Direct Volume Rendering via 3D Textures", 11 pages, University of California Santa Cruz, 1994. URL:http://citeseerx.ist.psu.edu/viewdoc/download?oi=10.1.1.53.3319&rep=rep1&type=pdf.
Ronghua Liang et al: "Fast Hardware-Accelerated Volume Rendering of CT Scans", Journal of Display Technology, IEEE Service Center, New York, NY, US, pp. 431-436, vol. 4, No. 4, Dec. 1, 2008.
Rezk-Salama C et al: "Interactive Volume Rendering on Standard PC Graphics Hardware Using Multi-Textures and Multi-Stage Rasterization", 10 pages, Proceedings 2000 Siggraph/Eurographics Workshop on Graphics Hardware. Interlaken, Switzerland, Aug. 21, 2000.
Travis Gerkin: "Volume Rendering using Graphics Hardware", 54 pages, GPU Programming and Architecture, URL: http://www.seas.upenn.edu/-cis565/LECTURES/VolumeRendering.pdf (retrieved on Nov. 23, 2015).
Office Action for corresponding CN Application No. 201280054856.6, 10 pages, dated Oct. 26, 2015.
Office Action for corresponding JP Application No. 2011-246279, dated May 12, 2015.
European Search Report for corresponding EP Application No. 12847428.5, 33 pages, dated May 3, 2016.
David S. Ebert et al, "Designing Effective Transfer Functions for Volume Rendering from Photographic Volumes", IEEE Transactions on Visualization and Computer Graphics, vol. 8, No. 2, pp. 183. (Jun. 2002).
Ghosh A et al., "Hardware assisted multichannel volume rendering" Center for Visual Computing (CVC) and Computer Science Department. Proceedings of the Computer Graphics International, IEEE, p. 1-6, (Jul. 2003).
Honigmann D et al., "Adaptive design of a global opacity transfer function for a direct volume rendering of ultrasound lata," IEEE Visualization Proceedings, p. 489-496, (Jan. 2003).
Koo-Joo Kwon et al, "Visualization of segmented color volume data Using GPU", Advances in Artificial Reality and Tele-Existence. 16th International Conference. Proceedings, pp. 1062-1069 (Jan. 2006).
K. O Conor et al, "3D Visualisation of Confocal Fluorescence Microscopy Data", Fifth Irish Workshop on Computer Graphics (2004), Eurographics Irish Chapter (Editors) 6 pages, (Jan. 2004).
Matthew McAullife, "Chapter 11: Changing Image Datasets Using MIPAV Utilities" National Institutes of Health-Center for Information Technology: MIPAV MIPAV Users Guide, vol. 1, Basics pp. 400-490, (Oct. 15, 2011).
Meissner M et al., "Volume Visualization, and Volume Rendering Techniques" Eurographics 2000 Internet Citation, xPee2365866, Retrieved from the Internet: URL:http://www.gris.uni-tuebingen.de/people/staff/meissner/tutorials/tutorial.pdf, p. 1-36., (Jan. 2000).
Hui Y W et al. "3D cursors for volume rendering applications", Nuclear Science Symposium and Medical Imaging conference, IEEE Conference, pp. 1243-1245, (Oct. 1992).
Gelder Van A et al: "Direct Volume Rendering With Shading Via a Three-Dimensional Textures", Proceedings of the 1996 Symposium on Volume Visualization, IEEE, San Francisco, Oct. 28-29, 1996; [Proceedings of the Symposium on Volume Visualization], pp. 23-30, (Oct. 28, 1996).
Joe Kniss et al, "InteractiveTexture-Based volume Rendering for Large Data Sets", University of Utah, IEEE Computer Graphics and Applications, pp. 52-61 (Jul.-Aug. 2001).
Office Action for corresponding Chinese Application No. 201280054856.6, 21 pages, dated Jun. 20, 2016.

* cited by examiner

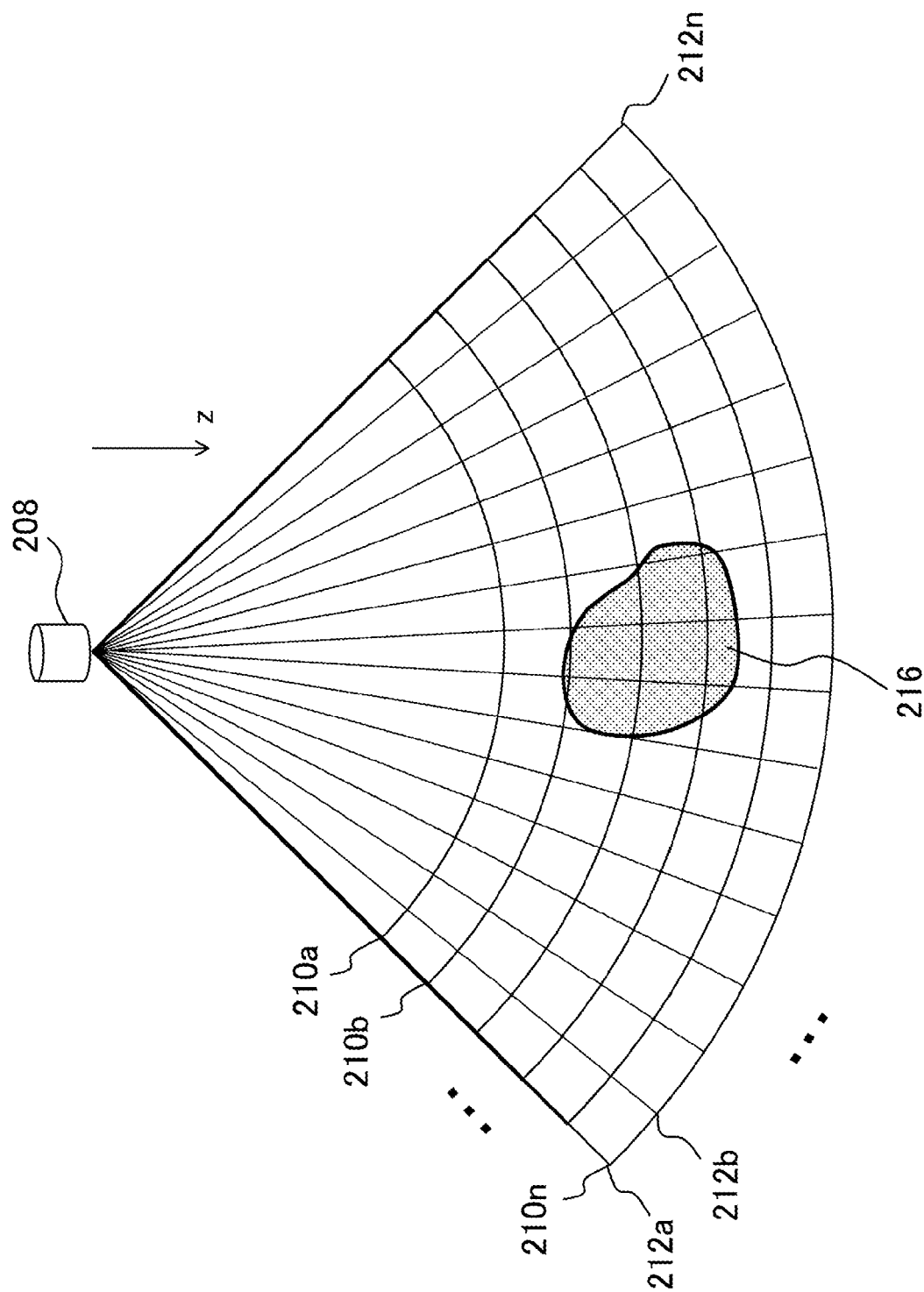

IMAGE PROCESSING APPARATUS, IMAGE PROCESSING METHOD AND DATA STRUCTURE OF IMAGE FILE

TECHNICAL FIELD

The present invention relates to an image processing apparatus for visualizing information on a target object as an image and to an image processing method used in the apparatus.

BACKGROUND ART

A technique of obtaining information regarding a cross-sectional shape or contents of a target object using electron beams, X-rays, magnetic fields, or the like has been put into practical use in transmission electron microscopes, CT (Computed Tomography), MRI (Magnetic Resonance Image), and the like. In this technique, information on each cross-section of a target object is acquired in an axial direction that is perpendicular to the cross-section and can be stored as layered image information of the entire target object. Layered image information is not limited to those obtained by a relatively large-scale apparatus such as the one described above and can be also obtained by a cross-sectional shape measuring apparatus or the like that used visible light, laser, or the like.

DISCLOSURE OF THE INVENTION

Problem to be Solved by the Invention

Information obtained in a technique such as the one described above is information in a three-dimensional space formed by a two-dimensional plane that constitutes a cross-section and an axis that is perpendicular to the cross-section. Thus, it is difficult to visualize such information as a commonly-used two-dimensional image in an easily understandable way. The simplest way possible is to display two-dimensional information regarding a cross-section while changing a position in the axial direction. However, in this case, it is difficult to understand the size or position of a target object in the axial direction. A method of acquiring data for each voxel so as to perform volume rendering has also been put into practical use. However, there are also problems that a load of resources or processes that are required for data acquisition, storage, and image rendering is increased and that the degree of freedom for data processing and operations is low as well.

In this background, a purpose of the present invention is to provide an image processing technique for easily visualizing layered image information.

Means to Solve the Problem

One embodiment of the present invention relates to an image processing apparatus. This image processing apparatus includes: a data acquisition unit configured to acquire distribution information of values obtained on a plurality of slice surfaces that intersect at the same angle with a predetermined axis at different positions on the predetermined axis; a slice image generation unit configured to generate, for each of the slice surfaces, a slice image that expresses the distribution information as an image by determining a pixel value that includes an alpha value based on a value at each position on the slice surfaces; and an image drawing unit configured to display, as a three-dimensional object, a three-dimensional space that is formed by the plurality of slice surfaces by arranging the slice image at a corresponding position on the axis and performing alpha blending drawing according to the position of a viewpoint that is input.

The "values obtained on a plurality of slice surfaces" may be values that are actually measured by a sensor or the like or values obtained by performing some kind of calculation on the values that are measured. Alternatively, the values may be calculated values that are computed by a CAD (Computer Aided Design), a game, or the like. Therefore, the "slice surfaces" may be plane surfaces or curved surfaces in an actual space or may be plane surfaces or curved surfaces in a virtual space.

Another embodiment of the present invention also relates to an image processing apparatus. This image processing apparatus includes: a slice image storage unit configured to store data of a slice image that is generated, regarding distribution information of values obtained on a plurality of slice surfaces that intersect at the same angle with a predetermined axis at different positions on the predetermined axis, by determining a pixel value including an alpha value based on a value at each position on the slice surfaces and that expresses the distribution information as an image; a slice image management unit configured to load the data of the slice image from the slice image storage unit into memory for drawing according to the position of a viewpoint that is input; and an image drawing unit configured to display, as a three-dimensional object, a three-dimensional space that is formed by the plurality of slice surfaces by arranging the slice image at a corresponding position on the axis and performing alpha blending drawing in order of loading into the memory for drawing in parallel with a process of the loading by the slice image management unit.

Yet another embodiment of the present invention relates to an image processing method. This image processing method includes: acquiring distribution information of values obtained on a plurality of slice surfaces that intersect at the same angle with a predetermined axis at different positions on the predetermined axis in an image processing apparatus; generating, for each of the slice surfaces, data of a slice image that expresses the distribution information as an image by determining a pixel value that includes an alpha value based on a value at each position on the slice surfaces; and displaying on a display apparatus, as a three-dimensional object, a three-dimensional space that is formed by the plurality of slice surfaces by arranging each slice image at a corresponding position on the axis and performing alpha blending drawing according to the position of a viewpoint that is input by an input apparatus.

Still another embodiment of the present invention relates to a data structure of an image file. This data structure of an image file associates data of a slice image that is generated, regarding distribution information of values obtained on a plurality of slice surfaces that intersect at the same angle with a predetermined axis at different positions on the predetermined axis, by determining a pixel value including an alpha value based on a value at each position on the slice surfaces and that expresses the distribution information as an image with the direction of the axis and the positions on the axis, and is loaded into memory in order to display on a display apparatus, as a three-dimensional object, a three-dimensional space that is formed by the plurality of slice surfaces by arranging the slice image at a corresponding position on the axis and performing alpha blending drawing according to the position of a viewpoint that is input in an image processing apparatus.

Optional combinations of the aforementioned constituting elements, and implementations of the invention in the form of methods, apparatuses, systems, and computer programs may also be practiced as additional modes of the present invention.

Advantage of the Invention

According to the present invention, layered image information can be visualized easily in a form desired by a user at a low resource cost.

BRIEF DESCRIPTION OF THE DRAWINGS

FIG. 18 is a diagram for schematically illustrating the shape of a slice image when distribution with respect to a partially cylindrical curved surface or a partially spherical surface is measured in the present embodiment.

BEST MODE FOR CARRYING OUT THE INVENTION

Figure 1:
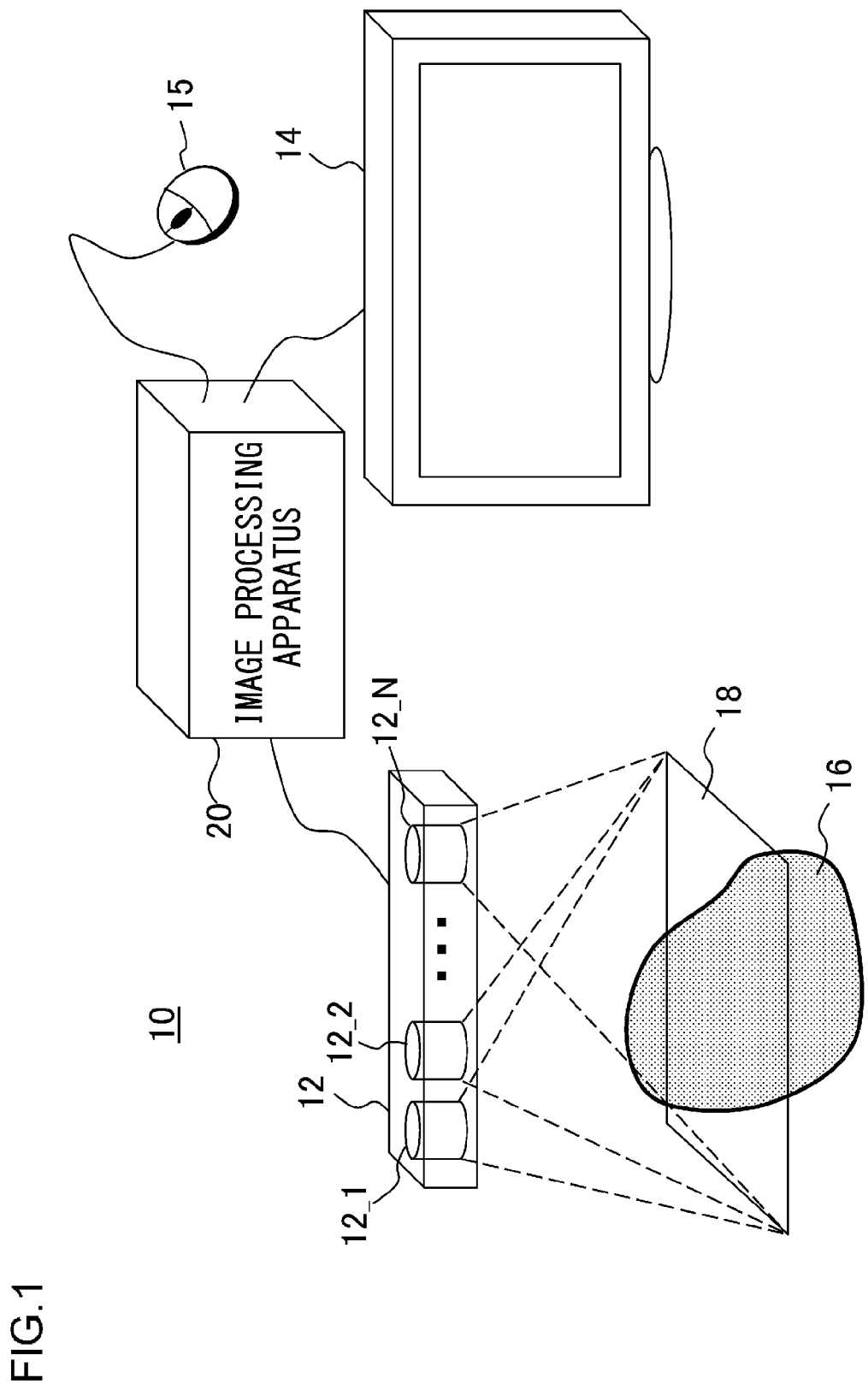
FIG. 1 is a diagram illustrating a configuration example of an image processing system to which an image processing technique according to a present embodiment can be applied.

FIG. 1 illustrates a configuration example of an image processing system to which an image processing technique according to a present embodiment can be applied. An image processing system 10 includes a sensor group 12 of N sensors composed of sensors 12_1, 12_2, . . . , 12_N each performing predetermined measurement, an image processing apparatus 20 for acquiring a measurement result from each of the sensors and visualizing the measurement result, an input apparatus 15 for a user to enter instruction input to the image processing apparatus 20, and a display apparatus 14 for displaying an image generated by the image processing apparatus 20.

The image processing apparatus 20 may be connected to the sensor group 12 and to the display apparatus 14 via wired cables or may be connected wirelessly via a wireless LAN (Local Area Network) or the like. Any two of or all of the sensor group 12, the image processing apparatus 20, and the display apparatus 14 may be integrally provided.

As described later, a process performed by the image processing apparatus 20 includes a stage of generating basic two-dimensional image data from a measurement result and a stage of generating a display image from the two-dimensional image data. Since these stages can be performed independently, the image processing apparatus 20, the sensor group 12, and the display apparatus 14 do not need to be connected all at the same time. The display apparatus 14 may be an apparatus that displays an image by itself such as a liquid crystal display or a plasma display or may be a combination of a projector and a screen for projecting an image, or the like.

The N sensors 12_1, 12_2, . . . , 12_N each acquire a predetermined physical quantity as distribution in a plurality of plane surfaces at a predetermined position and direction such as a plane surface 18 crossing a target object 16. The predetermined physical quantity means information such as color, temperature, contained water, hardness, and the like that can be obtained using visible light, X-rays, magnetism, electricity, ultrasonic waves, or the like by a commonly-used sensing technique, and the type thereof is not limited. In the figure, the arrangement and shape of the sensors 12_1, 12_2, . . . , 12_N are listed merely as an example, and a person skilled in the art should appreciate that there are various possible modes depending on a sensing technique that is used.

The image processing apparatus 20 unifies distribution of physical quantities in the plurality of plane surfaces measured by the sensor group 12 and visualizes, as a three-dimensional object, a measurement space in which the plane surfaces are layered. The object can be viewed from an arbitrary direction in accordance with a request for moving a viewpoint received from a user via the input apparatus 15. In addition to this, the image processing apparatus 20 controls the entire image processing system 10 in an integrated manner such as controlling a plane surface for which the sensor group 12 acquires a physical quantity and controlling display in the display apparatus 14.

A sensing apparatus that includes the sensor group 12 and has a mechanism for controlling a measurement process by the sensors and output of layered image information may be introduced separately from the image processing apparatus 20. The sensing apparatus may image, inside the apparatus, the distribution of physical quantities measured by the sensors, and the image processing apparatus 20 may acquire image data thereof. In this case, the distribution of pixel values of RGB or the like is obtained instead of the physical quantities measured by the sensors. Such pixel values are also treated in the same way as "physical quantity" in the following explanations.

The display apparatus 14 displays an image including the three-dimensional object generated as a result of the visualization of the distribution of the physical quantities by the image processing apparatus 20. As described above, in addition to a request for moving a viewpoint with respect to the three-dimensional object displayed on the display apparatus 14, the input apparatus 15 receives requests from the user such as requests for starting the measurement of physical quantities by the sensor group 12, starting the acquisition of a measurement result, starting the processing of an image or data, and starting the object display by the display apparatus 14 and notifies the image processing apparatus 20 of the requests. In addition to a mouse illustrated in the figure, the input apparatus 15 may be any one of commonly-used input apparatuses such as a keyboard, a controller, and a joystick or may be a touch panel or the like mounted on the screen of the display apparatus 14.

Figure 2:
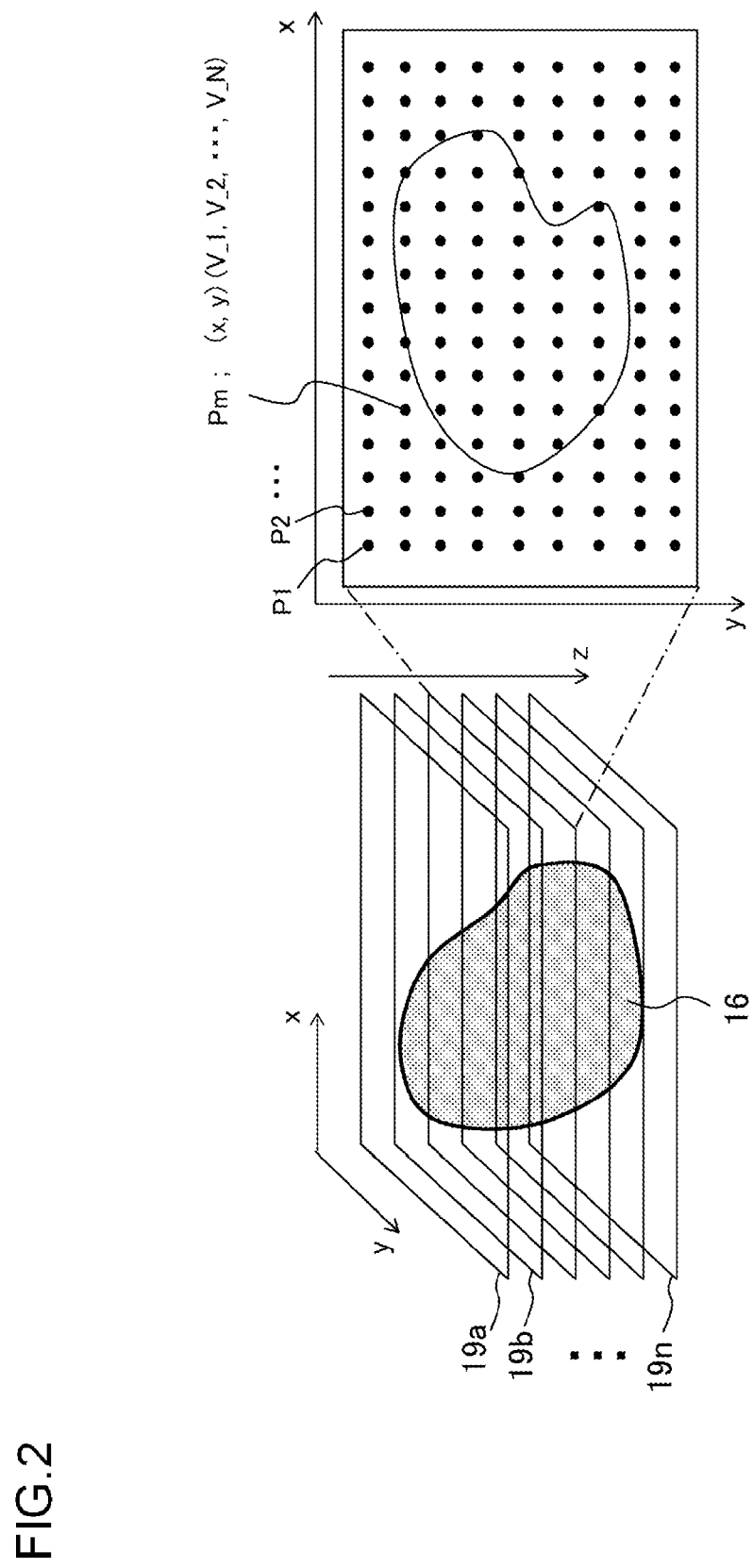
FIG. 2 is a diagram schematically illustrating the form of information acquired by an image processing apparatus as a result of measurement performed by a sensor group in the present embodiment.

FIG. 2 schematically illustrates the form of information acquired by the image processing apparatus 20 as a result of measurement performed by the sensor group 12. The sensors included in the sensor group 12 acquire the distribution of a predetermined physical quantity with respect to a plurality of plane surfaces 19$a$, 19$b$, . . . , 19$n$ perpendicular to a predetermined axis (z axis) as shown in the figure. The plane surfaces 19$a$, 19$b$, . . . , 19$n$ are located at different positions with respect to the z axis and are in the same range with respect to an xy plane surface that is perpendicular to the z axis.

Hereinafter, a direction for moving a plane surface for which the distribution of the physical quantity is acquired by the sensor group 12, just like the z axis in the figure, is referred to as "sensor axis," and the plane surface is referred to as "slice plane surface." The sensor group 12 may be provided such that a plurality of sensor axes can be set. In this case, a group of a plurality of slice plane surfaces is set for each of the sensor axes, and the distribution of the physical quantity is obtained for each of the plane surfaces. In FIG. 2, a slice plane surface is perpendicular to the sensor axis. However, the slice plane surface does not always need to be perpendicular depending on a physical quantity to be measured, the structure of a sensor, or the like.

The "distribution" can be obtained as a value for positional coordinates on each of such slice plane surfaces. Thus, when the sensor group 12 is composed of n sensors 12_1, 12_2, . . . , 12_N as shown in FIG. 1, n values are obtained for a given position on a given slice plane surface. As a result, information acquired by the image processing apparatus 20 is information associating respective positional coordinates (x,y) with respective vector values ($V\_1$, $V\_2$, . . . , $V\_N$) composed of n values for each of a plurality of positions P1, P2, . . . , set for each of the slice plane surfaces 19$a$, 19$b$, . . . , 19$n$.

The positions P1, P2, . . . , may be set at an interval of approximately a commonly-used pixel in practice. Depending on the resolution or the like of the sensors, it is appropriately designed that vector values of the same number of dimensions are obtained for each of the positions P1, P2, . . . by interpolating or thinning out measurement values. The sensor group 12 may repeat measurement at a predetermined time interval, and the image processing apparatus 20 may acquire the information shown in FIG. 2 at each point of time. In this case, a three-dimensional object that is displayed at the end represents a moving image that changes over the passage of time.

Figure 3:
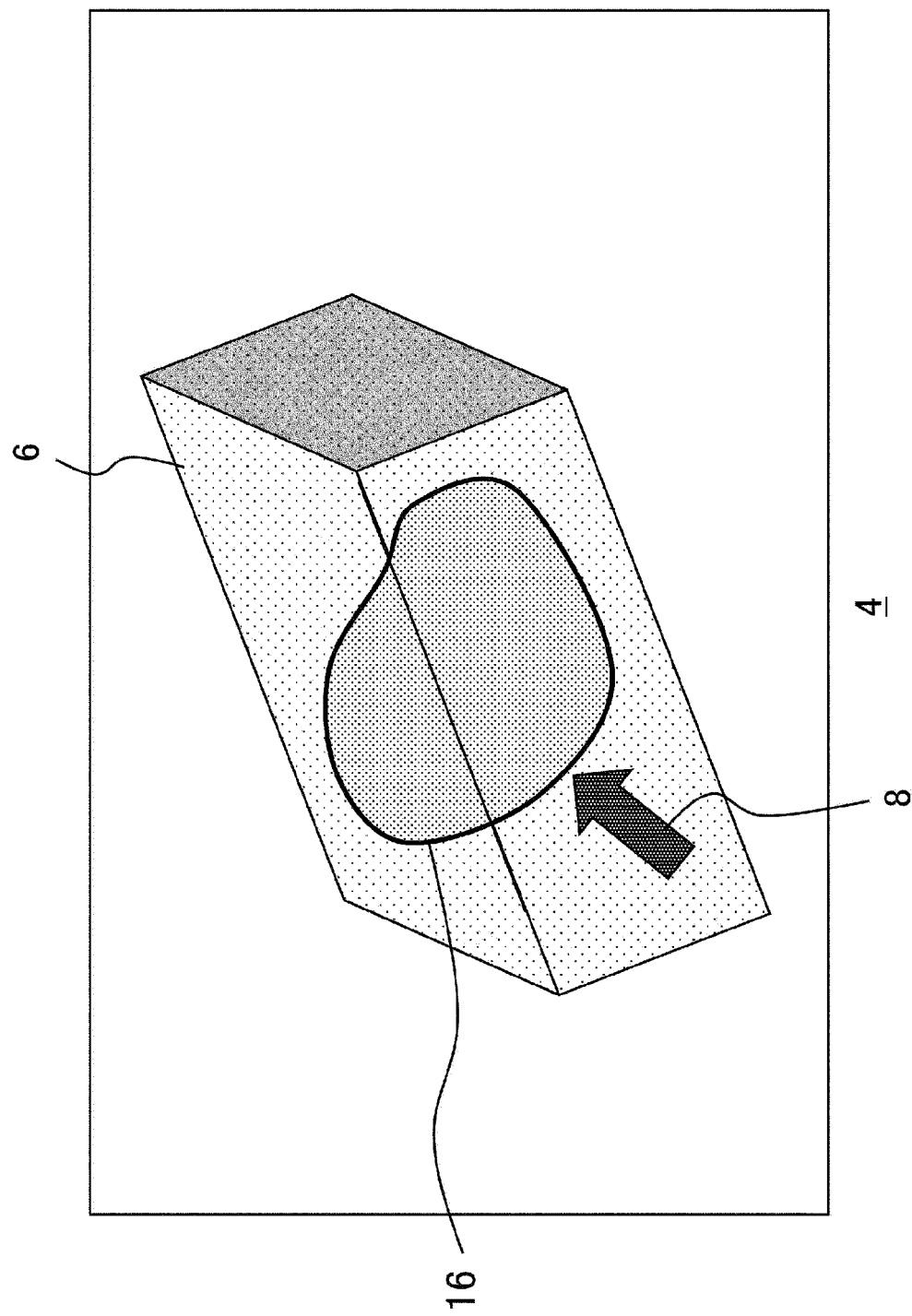
FIG. 3 is a diagram illustrating an example of an image generated by the image processing apparatus and displayed on a display apparatus in the present embodiment.

FIG. 3 illustrates an example of an image generated by the image processing apparatus 20 and displayed on the display apparatus 14. An image example 4 represents the visualization of measurement information shown in FIG. 2 and is displayed in a state where the target object 16 exists inside a three-dimensional object 6 indicating the measurement space. The user can move a virtual viewpoint by operating the input apparatus 15 and rotate the three-dimensional object 6 at a desired angle, thus allowing the back side and lateral side of the target object to be checked.

Further, by changing the transmittance of a desired area such as an area excluding the target object 16 or an area of the target object 16 in the three-dimensional object 6 by the operation by the user, the desired area can be changed to transparent or translucent. With this, even when there are a plurality of target objects, the respective positional relationships and sizes of those target objects can be observed from a desired direction. For example, when the three-dimensional object is displayed such that the area excluding the target object is transparent, the three-dimensional object is not visually observable, and only the target object becomes visually observable. In the following explanations, "three-dimensional object" also includes such a transparent area. When the three-dimensional object 6 is displayed as a moving image, the movement of the target object, the generation of a new target object, and the like are also observable. Also, an object, such as an arrow-shaped cursor 8, that is different from the measurement result can be displayed in a manner such that the object is displayed being inside the three-dimensional object 6.

Figure 4:
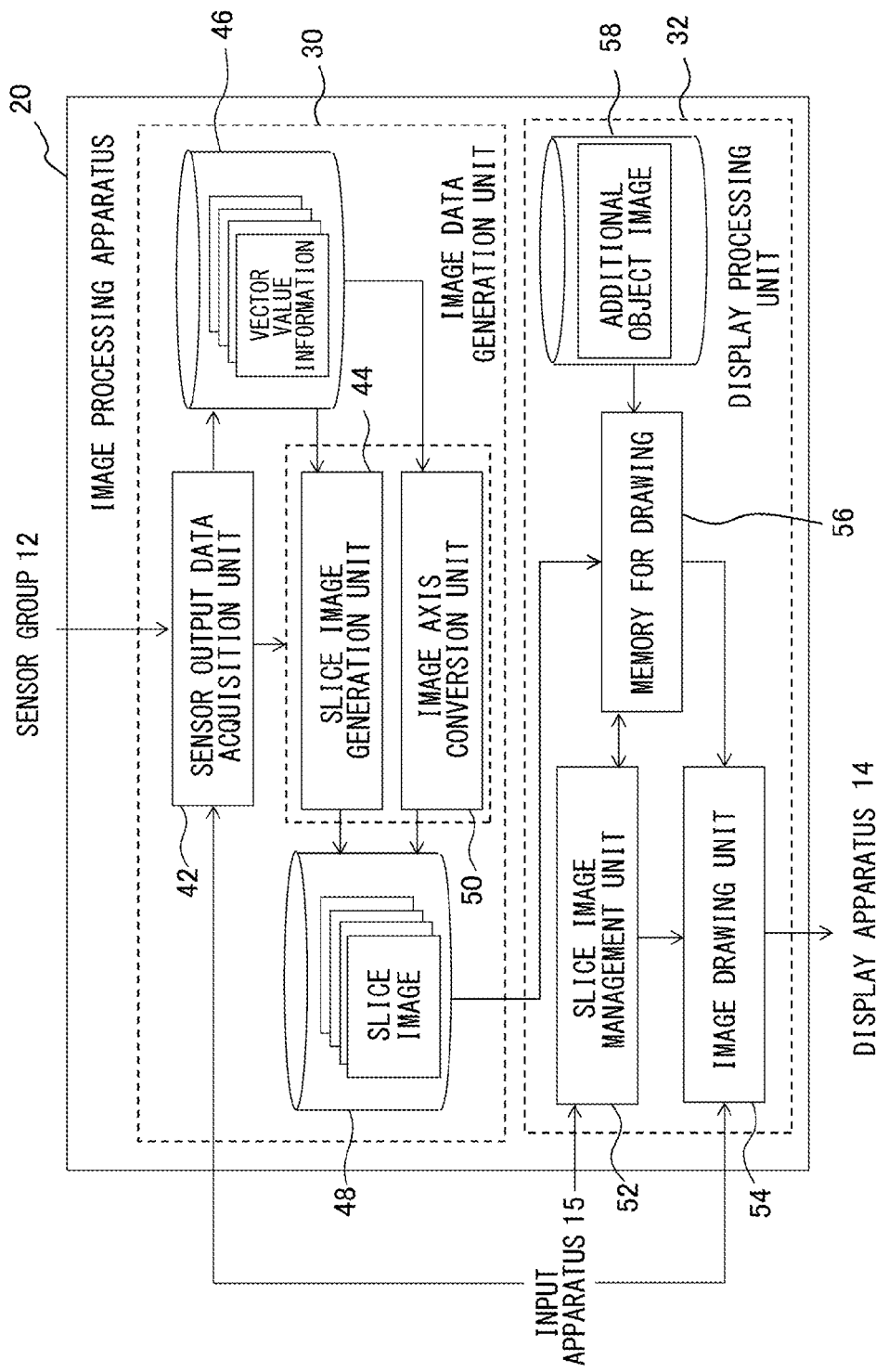
FIG. 4 is a diagram illustrating, in detail, the configuration of the image processing apparatus in the present embodiment.

FIG. 4 illustrates the configuration of the image processing apparatus 20 in detail. In FIG. 4, the elements shown in functional blocks that indicate a variety of processes are implemented in hardware by any CPU (Central Processing Unit), GPU (Graphics Processing Unit), memory, or other LSI's, and in software by a program for performing image processes, etc.

Thus, a person skilled in the art should appreciate that there are many ways of accomplishing these functional blocks in various forms in accordance with the components of hardware only, software only, or the combination of both, and the way of accomplishing these functional blocks is not limited to any particular one. As described above, the image processing apparatus 20 controls transmission and reception of data to and from another apparatus in the image processing system 10. Since a commonly-practiced technique can be applied to such a process, the illustration thereof is omitted in the figure.

The image processing apparatus 20 includes an image data generation unit 30 that acquires output information from the sensors and generates two-dimensional image data used for display, and a display processing unit 32 that draws a three-dimensional object using the two-dimensional image data. As described above, a process performed by the image data generation unit 30 and a process performed by the display processing unit 32 can be performed independently. Thus, both the image data generation unit 30 and the display processing unit 32 does not need to be provided in the same apparatus, and the image data generation unit 30 and the display processing unit 32 may be used as separate apparatuses that have respective functions.

The image data generation unit 30 includes a sensor output data acquisition unit 42 that acquires output data from the sensor group 12, a slice image generation unit 44 that generates data of a two-dimensional image for each slice plane surface in which distribution is acquired, an image axis conversion unit 50 that generates the similar data of a two-dimensional image for a plurality of plane surfaces having a predetermined angle with respect to an axis that is different from a sensor axis, a vector value information storage unit 46 that stores data generated by the sensor output data acquisition unit 42, and a slice image storage unit 48 that stores data generated by the slice image generation unit 44 and the image axis conversion unit 50.

The sensor output data acquisition unit 42 acquires distribution information of a physical quantity for each slice plane surface from the sensor group 12 and generates vector value information associating positional coordinates and a vector value as shown in FIG. 2. The sensor output data acquisition unit 42 temporarily stores the vector value information in the vector value information storage unit 46 in association with identification information of the slice plane surface and notifies the slice image generation unit 44 and the image axis conversion unit 50 accordingly. The identification information of the slice surface is constituted of the direction of the sensor axis, the position on the sensor axis, and the like.

Based on the vector value information stored in the vector value information storage unit 46, the slice image generation unit 44 generates, for each slice plane surface, data of a two-dimensional image used to generate a three-dimensional object. Hereinafter, such a two-dimensional image is referred to as "slice image." For each pixel, a slice image has an alpha value that indicates transmittance as well as information on a color space. By arranging a slice image in the direction of the sensor axis at the time of image display and performing alpha blending drawing, a three-dimensional object is expressed such that the inside of the three-dimensional object can be seen through. A detailed description will follow regarding a method of setting color space information and an alpha value. The slice image generation unit 44 stores generated data of a slice image in the slice image storage unit 48 in association with the identification information of the slice plane surface. There is also a method of calculating an alpha value based on the pixel value of a slice image. In this case, a drawing unit may calculate an alpha value and use the alpha value for blending, so that it becomes unnecessary to store the alpha value in a slice image storage unit.

The image axis conversion unit 50 generates a plurality of plane surfaces that have a predetermined angle to the predetermined axis other than the sensor axis, like an x axis and y axis that are orthogonal to the z axis when the z axis is the sensor axis as shown in FIG. 2, and generates vector value information similar to the one shown in FIG. 2 for each of the plane surfaces. In other words, by picking out values, from physical values on slice planes measured by the sensor group 12, which correspond to respective positions on the plane surfaces having direction different from the slice planes, the image axis conversion unit 50 reconstructs data as distribution for the plane surfaces.

Then, by a process similar to that performed by the slice image generation unit 44, the image axis conversion unit 50 generates data of a two-dimensional image that corresponds to each of the plane surfaces. Hereinafter, this two-dimensional image is also referred to as "slice image." However, the axis used with respect to the plane surfaces in this case is referred to as "image axis" in order to differentiate the axis from "sensor axis." The data of a slice image generated by the image axis conversion unit 50 is also stored in the slice image storage unit 48 in association with the direction of the image axis and the position on the axis.

The display processing unit 32 includes a slice image management unit 52 that manages a slice image used for drawing in accordance with the position of a viewpoint or the like, a memory 56 for drawing that sequentially stores data of image that is necessary for drawing, an additional object image storage unit 58 that stores image data of an object that is additionally displayed such as a cursor, and an image drawing unit 54 that draws a three-dimensional object using the data of a slice image.

The slice image management unit 52 switches an axis of a slice image to be used for drawing by moving a viewpoint and reads data of a necessary slice image from the slice image storage unit 48 into the memory 56 for drawing. When, for example, generating an object instantly from a slice image generated by the image data generation unit 30, the slice image storage unit 48 may also serve as the memory 56 for drawing. On the other hand, in a mode where all data of a slice image is stored in the slice image storage unit 48 that is installed in a secondary storage apparatus and where the data is loaded at another time at the time of display into the memory 56 for drawing, the slice image management unit 52 performs a drawing process while loading data gradually in the order necessary for drawing.

When drawing a three-dimensional object, slice images are basically superimposed by alpha blending process in order starting from the farthest from a viewpoint. Therefore, loading of slice image data into the memory 56 for drawing is also performed in the order basically. With this, latency to the time of display can be suppressed even when another slice image becomes necessary due to the movement of a viewpoint or the like. This loading process may be performed by a memory controller controlled by the slice image management unit 52.

The slice image management unit 52 further performs interpolation of slice images in accordance with a decrease in a distance between the viewpoint and the three-dimensional object. The slice images are generated for discrete positions on the sensor axis or the image axis, and the discontinuity thereof becomes visually recognizable as the viewpoint becomes closer to the object. Thus, the slice image management unit 52 generates a new slice image having a pixel value that interpolates pixel values of adjacent slice images with respect to a position on the axis. The slice image management unit 52 inserts the generated slice image between the original slice images so as to make the discontinuity less noticeable by reducing an interval between the slice images. The number of slice images to be inserted may be gradually increased in a manner inversely proportional to a distance to the viewpoint or may be increased in stages according to a comparison of the distance with a threshold value.

Upon acquiring a notification from the slice image management unit 52 indicating that the data of a necessary slice image has been loaded into the memory 56 for drawing, the image drawing unit 54 draws a three-dimensional object using this data. Basically, the image drawing unit 54 arranges the slice images at respective positions on the axis and performs superimposition by projecting the slice images onto screen coordinates in order starting from the farthest from a viewpoint. Regarding the three-dimensional object of a measurement space displayed in this way, for example, a space outside of a target object becomes transparent or translucent by the setting of an alpha value. The image drawing unit 54 further draws an additional object such as a cursor in such the space.

The user is allowed to move the additional object via the input apparatus 15 or move or generate the additional object while following the target object. Therefore, the image drawing unit 54 calculates a display position of the additional object in accordance with modes thereof and then reads out the data of the image into the memory 56 for drawing and draws the image. Further, the image drawing unit 54 may realize a stereoscopic view by performing a similar three-dimensional object drawing process for a plurality of viewpoints. The relative positions of the viewpoints or the like in this case can be appropriately determined according to a stereoscopic viewing method that is introduced.

Figure 5:
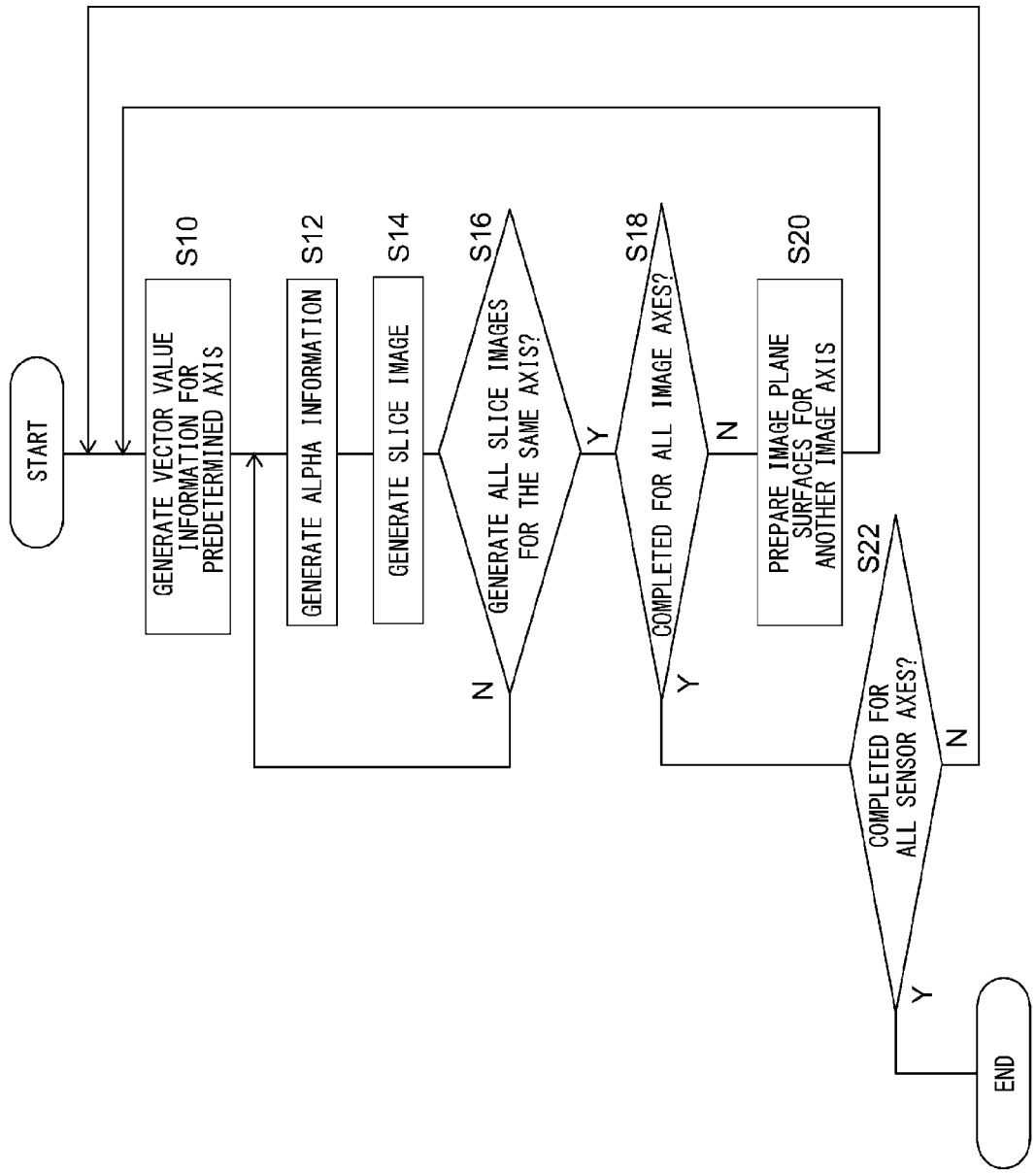
FIG. 5 is a flowchart illustrating a processing procedure for an image data generation unit to generate data of a slice image in the present embodiment.

An explanation will now be given of the operation of the image processing apparatus 20 that can be realized by such a configuration described above. FIG. 5 is a flowchart illustrating a processing procedure for the image data generation unit 30 to generate the data of a slice image. The sensor output data acquisition unit 42 first acquires, in accordance with an instruction from the user or the like, distribution of N physical quantities for a plurality of slice plane surfaces of the sensor axis from the sensor group 12 and generates vector value information associating positions on the respective plane surfaces and vector values composed of a set of the physical quantities (S10).

In this process, the vector values included in the vector value information may not be the N physical quantities themselves that are transmitted from the sensor group 12. For example, physical quantities that do not need to be taken into account in the information desired to be displayed at the end may be excluded from the elements. Alternatively, values obtained as a result of carrying out an operation by different physical quantities may be added as new elements. Also, masking by determination by a threshold value may be performed; for example, when a given physical quantity exceeds a threshold value, another physical value may be changed to zero. For example, this method is effective when, for example, displaying only a target object of a certain temperature or less.

A plurality of patterns may be generated for vector value information that can be obtained by manipulating measurement values as described above, and a target to be displayed may be switched by operation during the display. A specific processing rule of a physical quantity is, for example, determined by the user and stored as additional data in memory or the like that is not shown, and the sensor output data acquisition unit 42 refers to the processing rule at the time of generating vector value information.

The slice image generation unit 44 then determines an alpha value based on the vector values for each pixel in a two-dimensional array that is set for each of the slice plane surfaces (S12). A description will be made later regarding a specific method of determining an alpha value. By determining color information for each of the pixels based on the vector values, the slice image generation unit 44 further generates data of a slice image that stores the color information and the alpha value as a pixel value and stores the data in the slice image storage unit 48 (S14). The color system of the color information such as RGB, YCbCr, or the like is not limited. Also, as described above, when generating an alpha value from a slice image at the time of drawing in the image drawing unit 54, the alpha value does not need to be set in the slice image generation unit 44. Thus, the alpha value is not stored in the image storage unit 48.

The color information is determined in accordance with a rule that is set in advance according to the type of the physical quantity, a purpose of display, and the like. For example, RGB may be expressed using respective values measured by the three sensors 12_1, 12_2, and 12_3 as red color luminance, green color luminance, and blue color luminance, respectively. In this case, in a three-dimensional object that is displayed at the end, a red color, a green color, and a blue color strongly show up respectively in a material in which a physical quantity measured by the sensor 12_1 is large, in a material in which a physical quantity measured by the sensor 12_2 is large, and in a material in which a physical quantity measured by the sensor 12_3 is large, allowing for color classification according to the materials.

Alternatively, a single value that is measured by a certain sensor 12_1 may be substituted for all the R, G, and B, and the size of a physical quantity may be expressed by white color luminance. Rules for determining an alpha value and color information are appropriately determined by the user according to display contents, a purpose for display, and the like and are stored in memory or the like (not shown) in advance. Alternatively, the user may extemporarily set the rules via the input apparatus 15 while checking the actual display.

Until all the slice images for the sensor axis are generated, the slice image generation unit 44 repeats respective processes in S12 and S14 (N in S16, S12, and S14). Once all the slice images have been generated, the image axis conversion unit 50 prepares a plurality of slice plane surfaces for a predetermined image axis at respective positions where physical quantities have been obtained and generates, for each image axis, vector value information associating positions on the respective plane surfaces and vector values composed of a set of the physical quantities (Y in S16, N in S18, S20, and S10). The image axis conversion unit 50 then repeats a process of generating a slice image after determining an alpha value and color information for a pixel that is set on each of the plane surfaces and storing the slice image until all slice images for each of the axes are generated (S12, S14, and N in S16).

Once all slice images have been generated for all the image axes (Y in S18), the image axis conversion unit 50 repeats respective processes in S10 and S20 in an environment where a physical quantity can be acquired by another sensor axis (N in S22). Once slice images have been generated for all the sensor axes, the process is ended (Y in S22). In order to preferably draw a three-dimensional object that is to be displayed at the end in the present embodiment, slice images for three axes are desirably prepared. The simplest way possible is to generate slice images for an x axis, a y axis, and a z axis that are orthogonal to one another. Any one of these axes in three directions may be used as an image axis. Alternatively, an image axis may not be included.

In other words, as long as the axes in the three directions are measurable as sensor axes, the image axis conversion unit 50 does not need to perform the process. On the other hand, if a sensor axis is in only one direction, slice images for other image axes are generated by the image axis conversion unit 50, and branching in S22 no longer exists. If sensor axes are in two directions, the remaining single direction is used as an image axis, and the image axis conversion unit 50 generates slice images. As described, the setting of an image axis may be appropriately changed according to directions that can be set as sensor axes and the number thereof.

Figure 6:
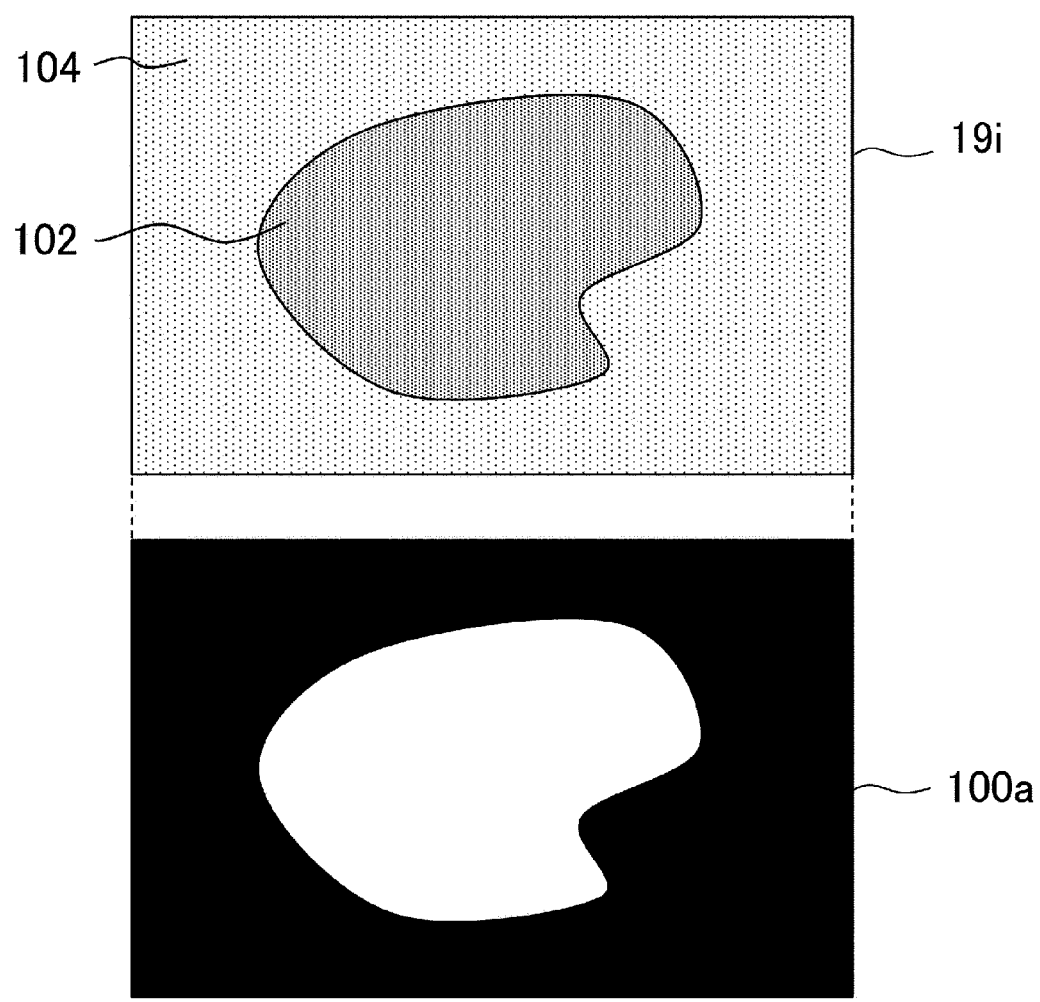
FIG. 6 is a diagram illustrating an example of a method of determining an alpha value of the slice image in S12 in FIG. 5.

FIG. 6 illustrates an example of a method of determining an alpha value of a slice image in S12 in FIG. 5. The upper side of the figure schematically shows vector value information in a slice plane surface 19*i*, and the lower side schematically shows an alpha value that is set in a corresponding slice image 100*a*. In the slice plane surface 19*i*, for example, in an area 102 where a target object exists and in the other area 104, at least either one of respective vector values changes greatly. In the figure, the difference thereof is indicated by two types of shadings.

In order to set an alpha value that reflects this difference, the following conditional branching is performed.

if max($V\_1, V\_2, \ldots, V\_N$)<Th $A=0$; else $A=1$;

In this conditional branching, Th represents a threshold value that is set in advance, and A represents an alpha value that is provided to each pixel. In other words, if the maximum value of the vector values ($V\_1, V\_2, \ldots, V\_N$) is smaller than the threshold value Th, the alpha value is set to be 0. If the maximum value is the threshold value Th or larger, the alpha value is set to be 1. In the slice image 100*a* in FIG. 6, the alpha value is shown to be 1 by a white color in the area 102, and the alpha value is shown to be 0 by a black color in the area 104. The positions at which the vector values are stored on the respective slice plane surfaces in the vector value information and positions that define respective pixels on the slice images may be different. In that case, the alpha value is determined at the former positions, and a value for each of the pixels is determined by appropriately interpolating an alpha value.

In the case of using a condition such as the one described above, when the types of physical quantities that constitute the vector values are different, all the values are normalized in advance in order to have the same scale. Conditional branching may be implemented after selecting a physical quantity used for branch determination. When an alpha value is provided by such conditional branching when including a physical quantity whose value becomes high in the range of a target object in the vector values, an area outside the target object becomes transparent, and an area including the target object becomes translucent. As a result, when a blending drawing is performed, display is shown where the far side can be seen through only behind the area outside the target object.

Figure 7:
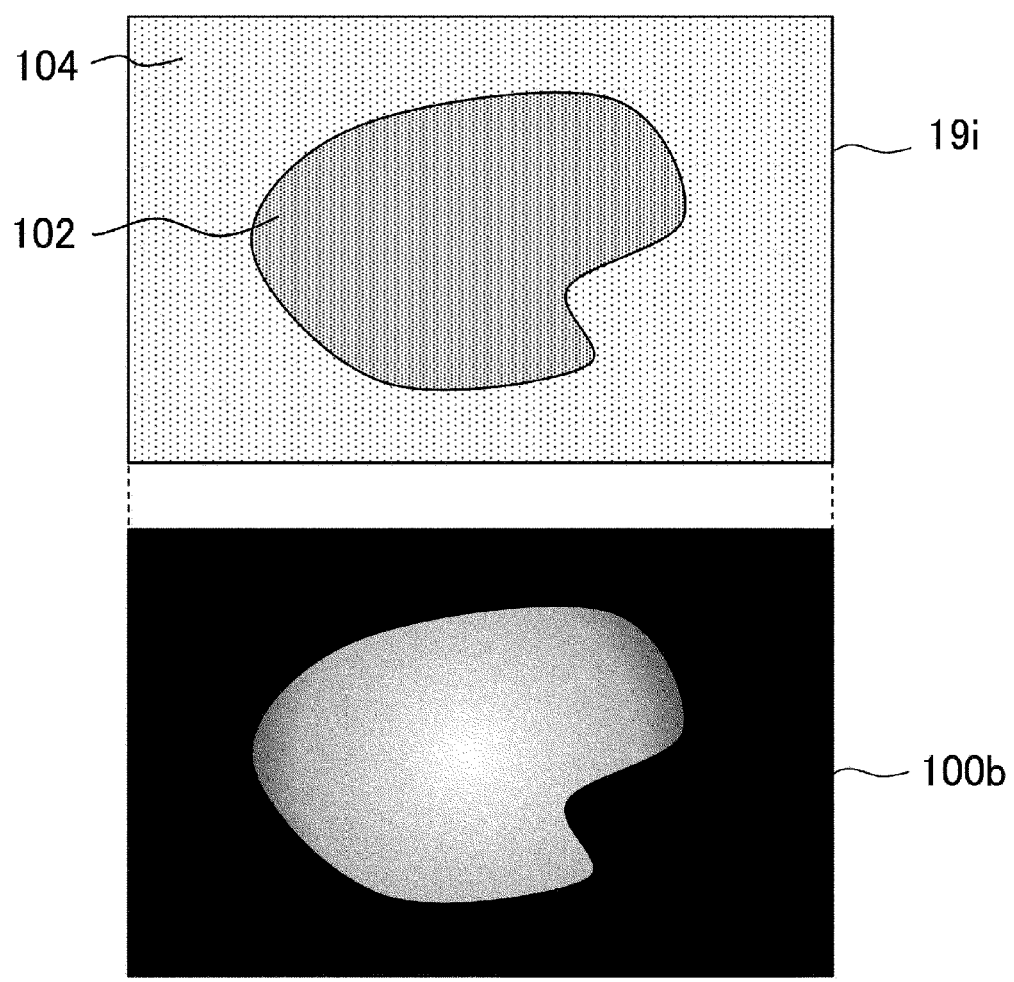
FIG. 7 is a diagram illustrating another example of a method of determining the alpha value of the slice image in S12 in FIG. 5.

FIG. 7 illustrates another example of a method of determining an alpha value of a slice image. The figure is expressed in the same way as in FIG. 6. Conditional branching in this case is set as follows:

if max($V\_1, V\_2, \ldots, V\_N$) < Th
   A = 0;
else      A = max($V\_1, V\_2, \ldots, V\_N$);

As in the case of FIG. 6, if the maximum value of the vector values ($V\_1, V\_2, \ldots, V\_N$) is smaller than the threshold value Th, the alpha value is set to be 0. However, if the maximum value is the threshold value Th or larger, the maximum value itself is used as the alpha value. In this case, the physical quantities that constitute the vector values are previously normalized. In a slice image 100*b* in the figure, gradation shows a change in a range of Th≤A≤1 of the alpha value in the area 102.

According to such conditional branching, for example, a change in a physical quantity inside a target object can be expressed by the transmittance of a color. Also, compared to the example shown in FIG. 6, the alpha value near the contour of the target object can be gradually changed. Thus, even when jaggies and noise are generated at the contour, the jaggies and the noise are less noticeable.

Besides this, there are various possible conditions for determining the alpha value from the vector values. For example, contrary to the case of FIG. 7, the following conditional branching may be set.

if max($V\_1, V\_2, \ldots, V\_N$) < Th
   A = max($V\_1, V\_2, \ldots, V\_N$);
Else     A = 1;

According to this setting, the alpha value can be changed according to the size of the physical quantities that constitute the vector values in the area outside a target object or the like. For example, the ambient temperature, the ambient humidity, and the like of the target object can be expressed by the transmittance of a color.

Further, by focusing only on a single physical quantity $V\_i$ of the physical quantities that constitute the vector values, the following conditional branching is also possible.

if $V\_i$ < Th
   A = 0;
   else     A = 1;
or
if $V\_i$ < Th
   A = 0;
   else     A = $V\_i$;

The above two types of conditional branching are the same as those shown in FIG. 6 and FIG. 7, except that the single physical quantity $V\_i$ is used for branching determination. For example, when a different physical quantity becomes large depending on a material, a material that is displayed as the target object can be switched by switching the physical quantity $V\_i$ that is used.

Further, two threshold values Th1 and Th2 (Th1<Th2) may be provided, and the following conditional branching may be set.

if max($V\_1, V\_2, \ldots, V\_N$) < Th2 || min($V\_1, V\_2, \ldots, V\_N$) > Th1
   A = 0;
   else     A = 1;

In other words, if the maximum value of the vector values ($V\_1, V\_2, \ldots, V\_N$) is smaller than the threshold value Th2 (the larger threshold value) or if the minimum value is larger than the threshold value Th1 (the smaller threshold value), i.e., if the vector values are within a predetermined intermediate range, transparentizing is performed while setting the alpha value to be 0. This example can be applied in a case where in a situation where a physical quantity acquired by a given sensor becomes smaller and where a physical quantity acquired by another sensor becomes larger in the area of a target object, all of those are desired to be displayed as the target object if any one of the sensors reacts.

Figure 8:
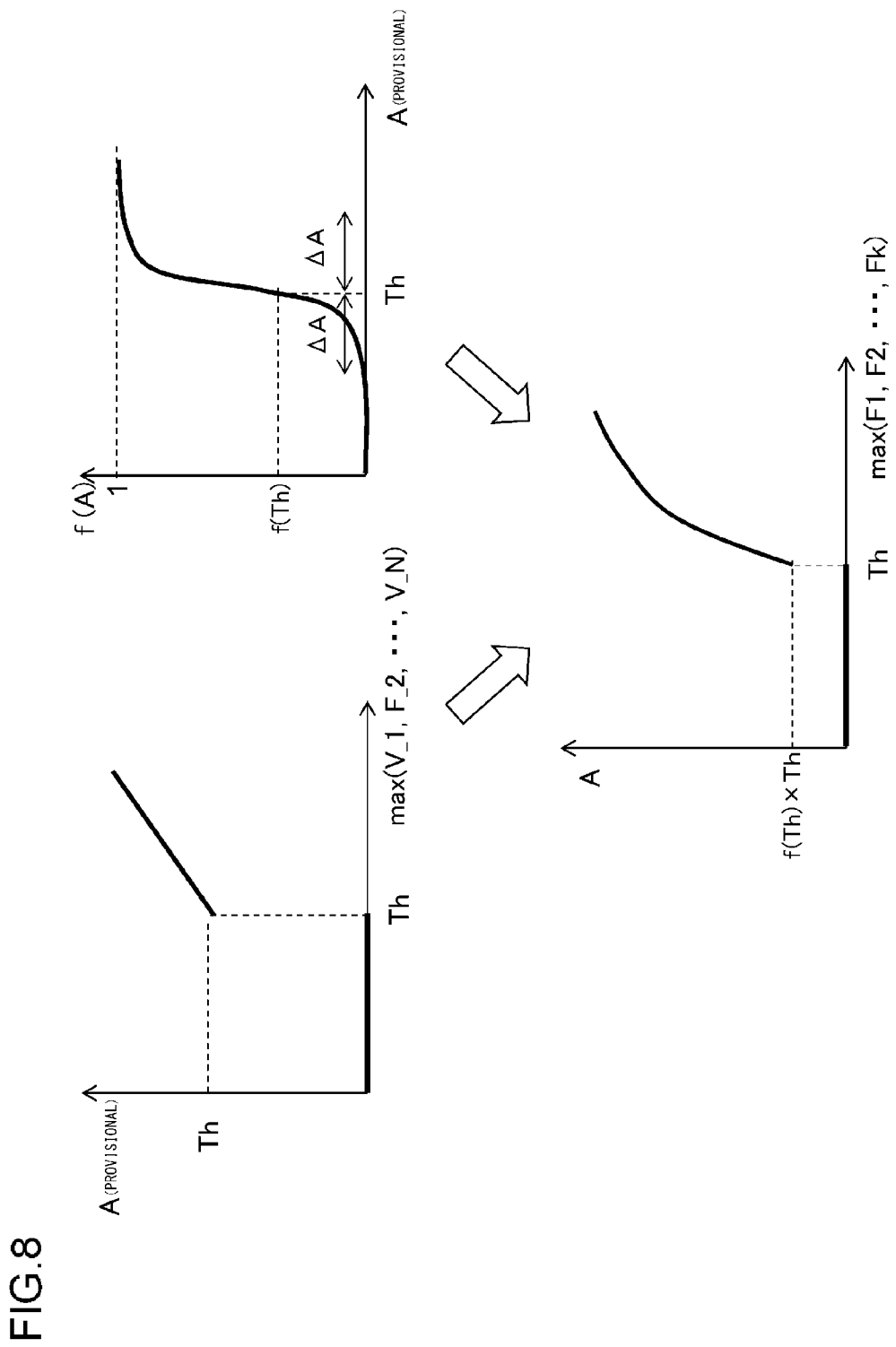
FIG. 8 is a diagram for explaining a method of suppressing the generation of noise in the setting of the alpha value in the present embodiment.

In a case where the setting of an alpha value is branched according to a magnitude relationship between the threshold value Th and the maximum value of the vector values as shown in FIG. 6 and FIG. 7, noise is likely to be caused at the time of display for a part where the maximum value is close to the threshold value Th, such as a part near the contour of the target object, since only a slight change in the vector values results in a large change in the setting of the alpha value. FIG. 8 is a diagram for explaining a method of suppressing the generation of such noise in the setting of the alpha value.

An upper left graph shows the maximum value of the vector values in the horizontal axis and an alpha value A determined by the conditional branching shown in reference to FIG. 7 in the vertical axis. In this method, a final alpha value A is determined by converting the alpha value determined by the conditional branching by a predetermined rule. Therefore, the alpha value shown in the graph is set to be a provisional value as shown in the figure. As shown in the graph, when the maximum value of the vector values is smaller than the threshold value Th, the provisional value of the alpha value A is 0. When the maximum value becomes equal to the threshold value Th, the provisional value of the alpha value A becomes the maximum value Th.

In order to prevent such a drastic change in the alpha value, the final alpha value A is calculated by operating a function f(A) such as the one shown in the upper right of the figure. The function f(A) is, for example, a function that gradually rises from 0 in a provisional value of the alpha value that is smaller than the threshold value Th by the amount of a predetermined width ΔA and further reaches 1 while the provisional value becomes larger than the threshold value Th by the amount of the predetermined width ΔA. Multiplication of a value obtained by such a function to the provisional value of the alpha value A results in a graph such as the one shown in the bottom of the figure.

In other words, when the maximum value of the vector values shown in the horizontal axis is smaller than the threshold value Th, the alpha value A is 0 as in the case of the provisional value. When the maximum value becomes equal to the threshold value Th, the alpha value A is suppressed to be smaller than the provisional value as a result of the multiplication of f(Th) to the provisional value Th. As a result, the alpha value no longer changes dramatically by a slight change in the maximum value of the vector values. The function f(A) is optimized in advance according to the rate of occurrence of noise in the actual display image or the like. A value that is output after substituting the provisional value of the alpha value A for the function f may be set to be the alpha value A.

The method of setting an alpha value shown thus far is a relatively simple method that is based on conditional branching. If it is desired to set an alpha value using a more complicated scheme, the alpha value may be prepared in advance for positional coordinates in an N-dimensional space formed by N physical quantities that constitute vector values. For example, when an alpha value is set using a different threshold value for each of physical quantities that constitute the vector values, it is possible that conditional branching becomes complicated.

Thus, a table is prepared in advance that associates alpha values for all conditions with positional coordinates in an N-dimensional space, i.e., combinations of N values. This allows an alpha value to be directly retrieved from a vector value only by referring to the table without going through a process of conditional branching or the like.

In a case, for example, where a predetermined function is calculated using, as a variable, any one of or a combination of the physical quantities that constitute the vector values and where an alpha value is determined using a result thereof, alpha values are calculated in advance for all the combinations of N values of the vector values and prepared as a table in the same way. This allows for a reduction in a processing load and in the amount of time required until the determination even when an alpha value is obtained using a complicated scheme.

Figure 9:
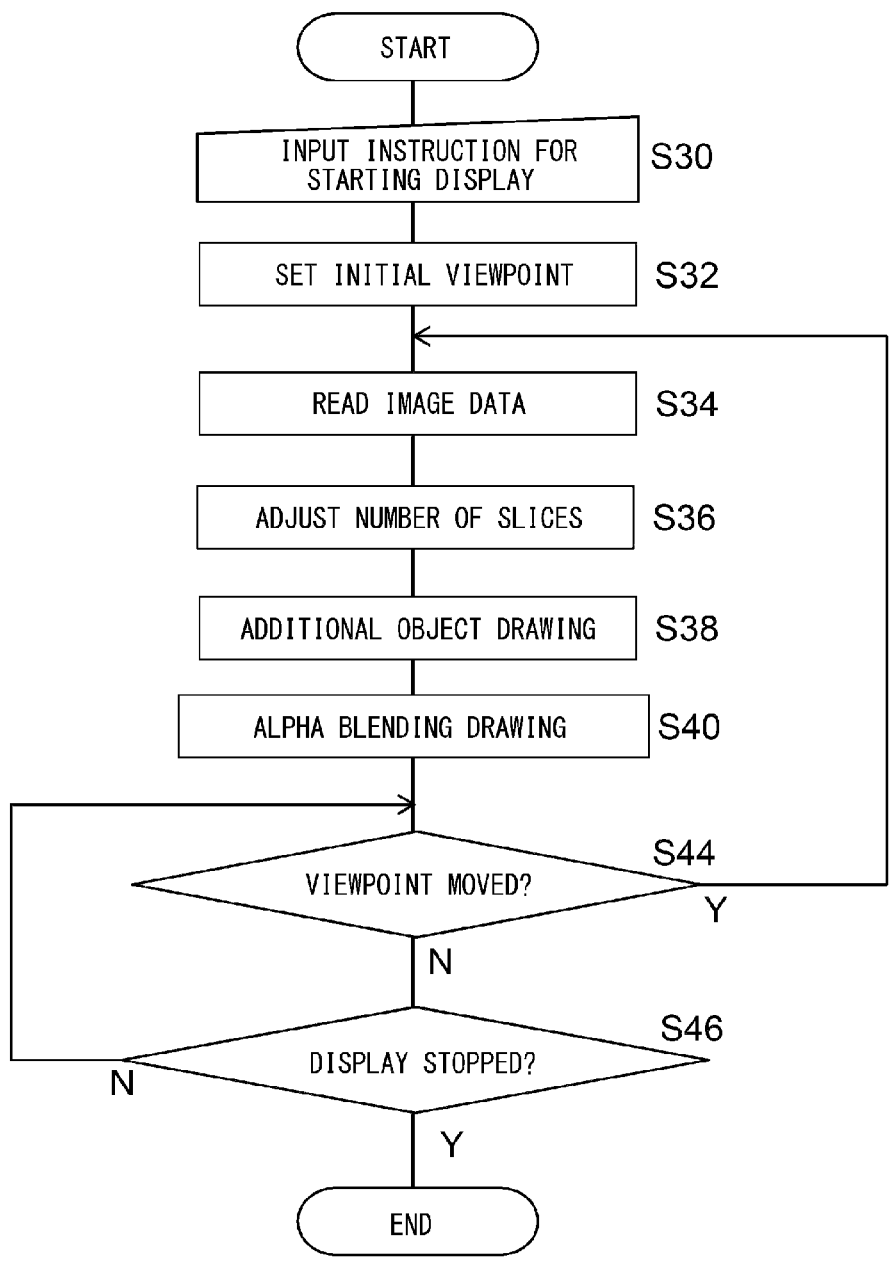
FIG. 9 is a flowchart illustrating a processing procedure for a display processing unit to perform a display process of a three-dimensional object in the present embodiment.

FIG. 9 is a flowchart illustrating a processing procedure for the display processing unit 32 to perform a display process of a three-dimensional object. First, when the user inputs an instruction for starting display via the input apparatus 15 (S30), the slice image management unit 52 sets, as an initial viewpoint, viewpoint coordinates that are set in advance for displaying an initial image of the three-dimensional object and loads data of a slice image necessary for drawing the three-dimensional object from the viewpoint into the memory 56 for drawing (S32, S34). In practice, a subsequent object drawing process can be performed in parallel by loading slice images in order of necessity as described above.

Then, the slice image management unit 52 adjusts the number of the slice images in accordance with a distance between the viewpoint and the three-dimensional object (S36). When the slice image management unit 52 generates a new slice image for interpolation, the slice image management unit 52 stores the slice image in the memory 56 for drawing. In order to be able to identify the position of a destination for insertion, image data itself is inserted between respective pieces of data of preceding and following slice images or is associated with a position on the axis at this time.

Then, the image drawing unit 54 draws an additional object to be displayed inside the three-dimensional object in accordance with, e.g., instruction input provided from the user via the input apparatus 15 (S38). As described above, the additional object is a cursor moved by the operation by the user, a marker displayed in contact with the target object, a line showing a trajectory of the target object, or the like and is set to be selectable by the user. The image drawing unit 54 determines a position at which the additional object is displayed based on designation by the user, a contour line of the target object obtained by an edge extraction process, or the like and then draws the additional object using the image data loaded into the memory 56 for drawing.

Then, the image drawing unit 54 draws a three-dimensional object that shows a measurement space by superimposing slice images loaded into the memory 56 for drawing, by alpha blending in order starting from the farthest from the viewpoint (S40). As described later, the process of drawing the additional object in S38 may be performed at the same time as the alpha blending drawing in S40.

When the user performs an operation of moving the viewpoint using the input apparatus 15 (Y in S44), processes in S34 through S40 are repeated in response to changes in the viewpoint. As long as no operation for moving the viewpoint or stopping display is made, the display at that time is continued (N in S44, N in S46), and the process is ended when an operation for stopping the display is entered (Y in S46).

Figure 10:
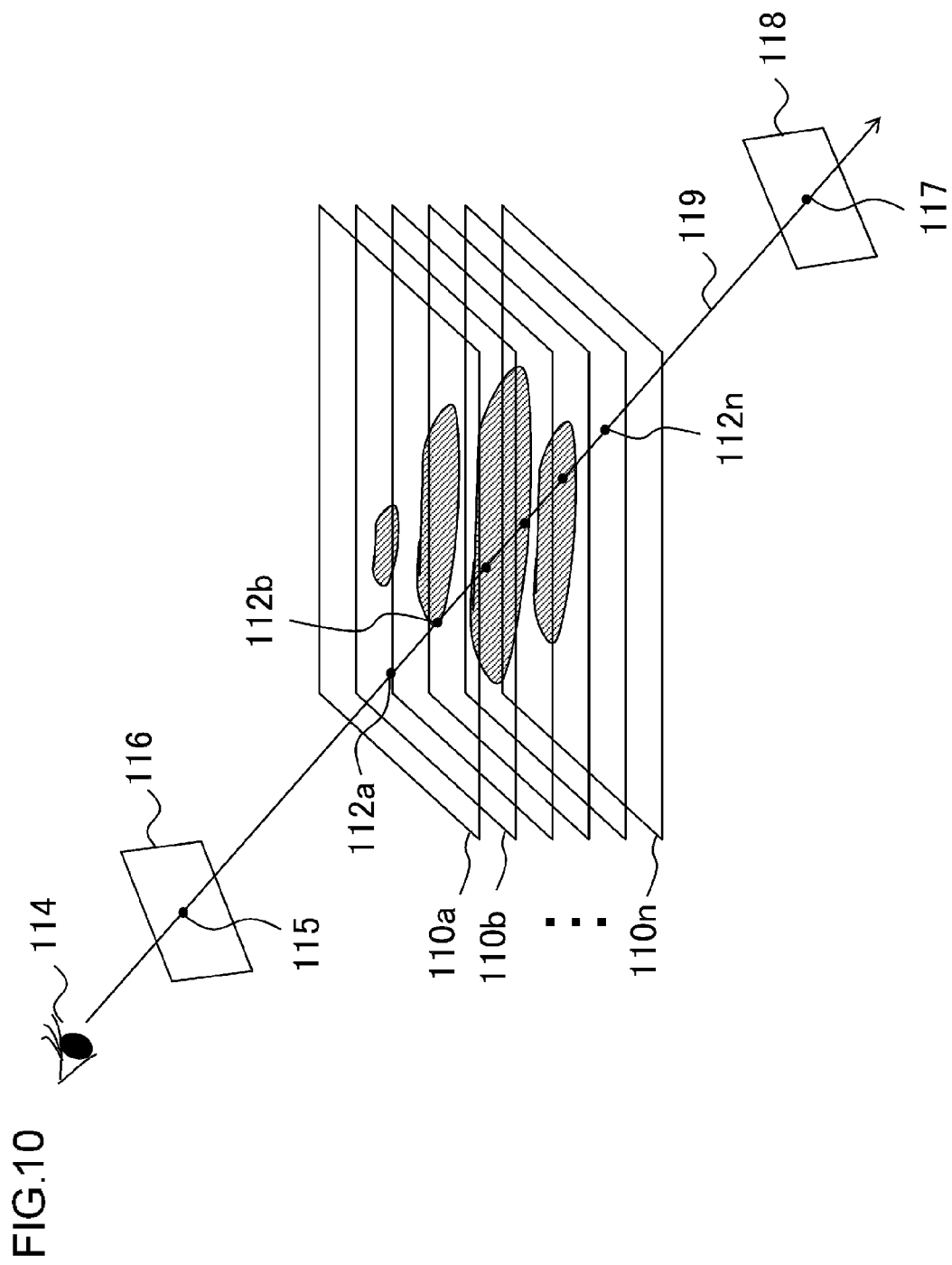
FIG. 10 is a diagram schematically illustrating the way an image drawing unit performs alpha blending drawing in S40 in FIG. 9.

FIG. 10 schematically illustrates the way the image drawing unit 54 performs alpha blending drawing in S40 in FIG. 9. In order starting from the closest to a viewpoint 114, a screen 116, slice images 110*a*, 110*b*, . . . , 110*n* that correspond to the object, and a background 118 are located. An image projected to a given point 115 on the screen 116 is superimposition of respective images of intersection points 112*a*, 112*b*, . . . , 112*n*, and 117 in order starting from the farthest from the viewpoint 114. The intersection points 112*a*, 112*b*, . . . , 112*n*, and 117 are points at the intersection of the line of sight 119 that passes the viewpoint 114 and a point 115 with the slice images 110a, 110b, . . . , 110n, and the background 118, respectively. In the case of the figure, the superimposition is performed in the order of the intersection points 117, 112n, . . . , 112b, and 112a.

Figure 11:
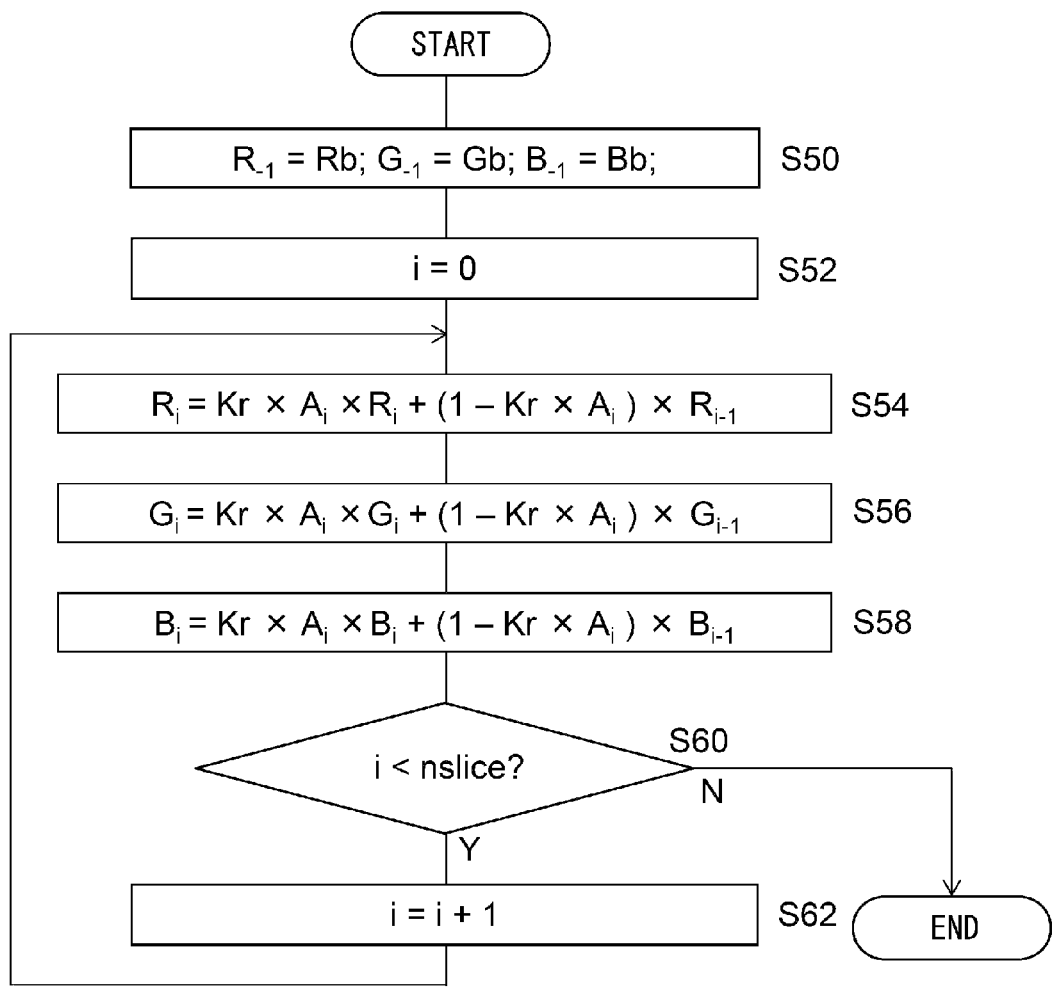
FIG. 11 is a flowchart illustrating a processing procedure for obtaining RGB values at a point on a screen in the present embodiment.

FIG. 11 is a flowchart illustrating a processing procedure for obtaining RGB values at the point 115 on the screen shown in FIG. 10. First, variables Ri, Gi, and Bi (i is an integer of −1 or more) are prepared, and RGB values, which are Rb, Gb, and Bb, at the intersection point 117 of the background 118 are substituted into $R_{-1}$, $G_{-1}$, and $B_{-1}$ (S50). When RGB values and an alpha value at the intersection point 112n on the slice image 110n, which is the farthest slice image from the viewpoint, are denoted as ($R_0$, $G_0$, $B_0$, $A_0$), respectively, RGB values obtained when the intersection point 117 of the background 118 and the intersection point 112n on the slice image 110n are superimposed on each other are as follows (S52, S54, S56, and S58).

$$R = Kr*A_0*R_0 + (1-Kr*A_0)*R_{-1}$$

$$G = Kg*A_0*G_0 + (1-Kg*A_0)*G_{-1}$$

$$B = Kb*A_0*B_0 + (1-Kb*A_0)*B_{-1} \quad \text{(Formula 1)}$$

In this case, Kr, Kg, and Kb are coefficients of the alpha value concerning red, green, and blue, respectively, when the alpha value held by a slice image is adjusted according to colors and are set in a range of 0<K<1 as necessary. When the adjustment according to colors is not necessary, Kr, Kg, and Kb satisfy Kr=Kg=Kb=1. By calculating for R, G, and B up to an intersection point of the last slice image (i=nslice−1) in order in a direction approaching to the viewpoint while using R, G, and B in the above expression as new $R_0$, $G_0$, $B_0$ and incrementing i (Y in S60 and S62), RGB values where all the respective intersection points of nslice pieces of slice images are superimposed can be obtained while allowing for a state of transparent and translucent (N in S60).

However, a processing procedure for drawing is not limited to this. For example, it is also possible to obtain the RGB values as follows. That is, when Formula 1 is generalized for RGB values obtained when slice images are superimposed up to (k+1)th slice image (i=k), the following is obtained.

$$R'_k = Kr*A_k*R_k + (1-Kr*A_k)*R'_{k-1}$$

$$G'_k = Kg*A_k*G_k + (1-Kg*A_k)*G'_{k-1}$$

$$B'_k = Kb*A_k*G_k + (1-Kb*A_k)*B'_{k-1} \quad \text{(Formula 2)}$$

In Formula 2, the RGB values after the superimposition are denoted as ($R'_k$, $G'_k$, $B'_k$) in order to differentiate from RGB values of ($R_k$, $G_k$, $B_k$) for only the (k+1)th slice image. If the final RGB values obtained when slice images are superimposed up to the last slice image (i=nslice−1) are expanded using the relationships in Expression 2 while going back to RGB values of the background, the final RGB values ($R'_{nslice-1}$, $G'_{nslice-1}$, $B'_{nslice-1}$) can be shown by a linear combination of RGB values for each slice image as follows:

$$R'_{nslice-1} = \sum_{-1}^{nslice-1} Br_i \times R_i \quad \text{(Formula 3)}$$

$$G'_{nslice-1} = \sum_{-1}^{nslice-1} Bg_i \times G_i$$

$$B'_{nslice-1} = \sum_{-1}^{nslice-1} Bb_i \times B_i$$

In the expression, ($Br_i$, $Bg_i$, $Bb_i$) are coefficients of RGB values ($R_i$, $G_i$, $B_i$) of an (i+1)th slice image, respectively, and are calculated from the alpha value of the slice image. Therefore, in a mode where alpha values of all slice images are determined before the drawing, the final RGB values may be calculated using Expression 3 after first obtaining the coefficients ($Br_i$, $Bg_i$, $Bb_i$) in accordance with the viewpoint.

Figure 12:
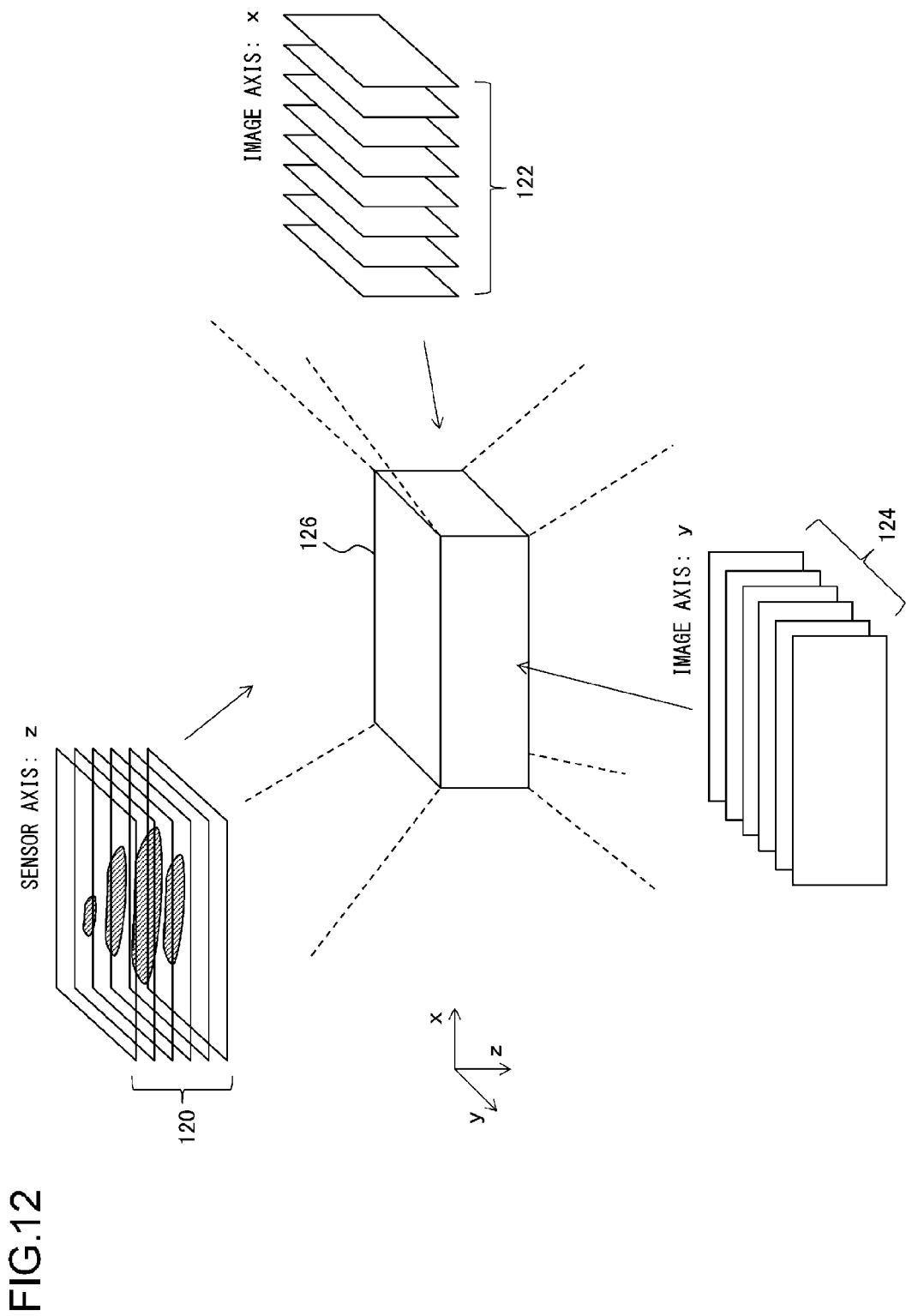
FIG. 12 is a diagram for explaining a process for a slice image management unit to determine data of a necessary slice image in accordance with a viewpoint in S34 in FIG. 9.

FIG. 12 is a diagram for explaining a process for the slice image management unit 52 to determine data of a necessary slice image in accordance with the viewpoint in S34 in FIG. 9. As described above, slice images are resultant of the imaging of distribution of physical quantities at discrete positions with respect to a predetermined axis. When the sensor axis is a z axis in a vertical direction of the figure, slice images that are generated are basically a plurality of parallel surfaces that constitute xy plane surfaces just like the slice image group 120. When displaying a three-dimensional object 126 viewed from the upper side or the lower side of the figure using the slice image group 120, an image with no sense of incongruity can be drawn by performing superimposition such as the one explained in FIG. 10.

Meanwhile, when the viewpoint is placed at a position near an x axis in a horizontal direction of the figure or a y axis in a depth direction, a space between slice images will become visible. Thus, as described above, slice image groups are generated for a plurality of axes by generating slice images for an image axis different from the sensor axis in advance, or by measuring physical quantities for a plurality of sensor axes in advance, and a slice image group that is used is switched by the movement of the viewpoint. In an example of the figure, a slice image group 122 using the x axis as the image axis and a slice image group 124 using the y axis as the image axis are prepared.

Then, a three-dimensional space around the three-dimensional object 126 to be displayed is divided, and a slice image group used for drawing is switched depending on which division the viewpoint is located. For example, as shown by dashed lines in the figure, boundary lines are set starting from respective vertices of the three-dimensional object 126. The boundary lines make a predetermined angle to three sides of the three-dimensional object 126, which form the respective vertices. A trapezoidal space having these boundary lines as lateral face sides thereof and a surface of the three-dimensional object as an upper surface thereof is defined to be a single division.

For example, when there is the viewpoint inside a division located at the upper surface or the lower surface of the three-dimensional object 126, the line of sight is closest to the z axis. Thus, the slice image group 120 using the z axis as an axis thereof is used for drawing. Similarly, when there is the viewpoint inside a division located at the left surface or the right surface of the three-dimensional object 126, the line of sight is closest to the x axis. Thus, the slice image group 122 using the x axis as an axis thereof is used for drawing. When there is the viewpoint inside a division located at the surface in front or the surface in the back of the three-dimensional object 126, the line of sight is closest to the y axis. Thus, the slice image group 124 using the y axis as an axis thereof is used for drawing.

Figure 13:
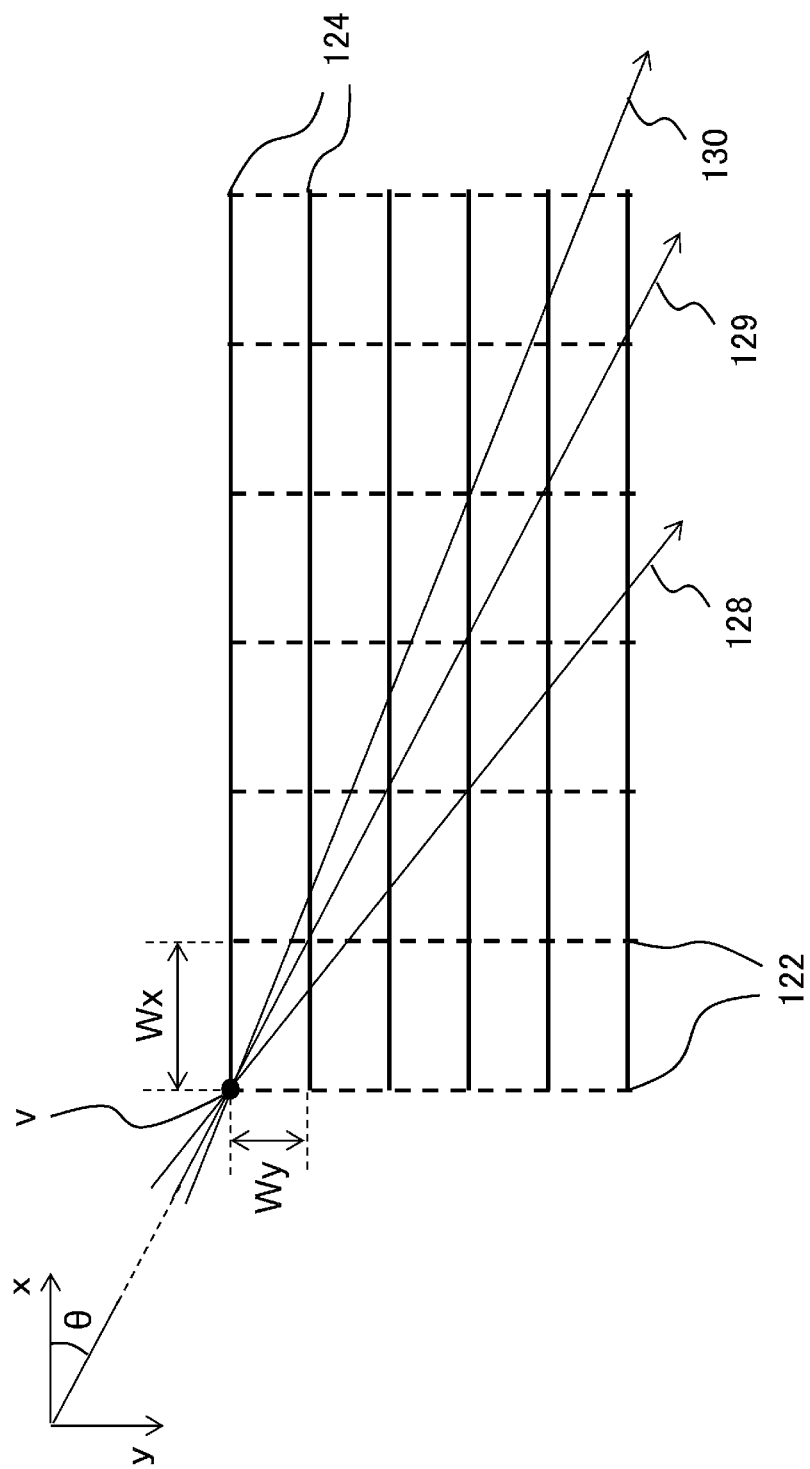
FIG. 13 is a diagram for explaining an example of a method for determining an angle of a boundary line for switching a slice image in the embodiment.

FIG. 13 is a diagram for explaining an example of a method for determining an angle of a boundary line. First, slice image groups that use two directions orthogonal to each other as axes thereof are taken into consideration. In the example of FIG. 12, both a slice image group that uses the x axis as an axis thereof and a slice image group that uses the y axis as an axis thereof are taking into consideration. In the figure, the slice image group 122 (dashed line) that uses the x axis as the axis thereof and the slice image group 124 (solid line) that uses the y axis as the axis thereof are arranged on the same xy plane surface and viewed from the z axis direction. In the figure, if the three-dimensional object is viewed from the upper left, the line of sight that passes through a vertex v changes as shown by an arrow 128, 129, or 130 depending on the position of the viewpoint.

The number of slice image groups that have points at the intersection with each line of sight is as follows in order of: (the slice image group 122 that uses the x axis as the axis thereof)/(the slice image group 124 that uses the y axis as the axis thereof).

line of sight for arrow 128: 4/6
line of sight for arrow 129: 6/6
line of sight for arrow 130: 7/6

This means that, in the line of sight for the arrow 129, the same number of alpha blending processes is performed when data of either of the slice image groups is used. Thus, the same display image is obtained. Therefore, by setting a boundary line in the direction of the arrow 129, display images before and after the switching are connected in a continuous manner. When an interval between the images of the slice image group 122 that uses the x axis as the axis thereof is denoted as Wx, and when an interval between the images of the slice image group 124 that uses the y axis as the axis thereof, an angle $\theta$ of the arrow 129 satisfies the following: $|\tan \theta|=Wy/Wx$. Thus, the slice image groups are switched according to the following conditions.

switch to slice image group that uses *y* axis as axis thereof when $|\tan \theta| \geq Wy/Wx$ switch to slice image group that uses *x* axis as axis thereof when $|\tan \theta| < Wy/Wx$ When the above conditions are expanded to three dimensions such that line-of-sight vectors are denoted as (X, Y, Z), respectively, and such that the slice image groups using the z axis, the x axis, and the y axis as the axes thereof are denoted as Sz, Sx, and Sy, respectively, the following switching conditions are obtained.

*Sz* when $|Z/X| \geq Wz/Wx$ and $|Z/Y| \geq Wz/Wy$

*Sx* when $|Z/X| < Wz/Wx$ and $|X/Y| \geq Wx/Wy$

*Sy* when $|Z/Y| < Wz/Wy$ and $|X/Y| < Wx/Wy$

The line-of-sight vectors that serve as boundaries of the above conditions correspond to the boundary lines shown by the dashed lines in FIG. 12. With this, even when the slice image groups used for display are switched according to changes in the viewpoint, the slice image groups can be seamlessly connected before and after switching. In the examples shown in FIG. 12 and FIG. 13, a sensor axis or an image axis is perpendicular to slice images. However, as described above, the present embodiment is not limited thereto. For example, in the case of a measurement system where a slice image is not perpendicular to a sensor axis, a slice image generated by the image axis conversion unit 50 by reconstructing the measurement value does not need to be perpendicular to the image axis, either. The sensor axis and the image axis do not need to be orthogonal to each other. In these cases, a boundary line can be also set based on the same theory as the one described above, and the same applies to a process of switching slice images according to the viewpoint and performing alpha blending drawing.

Figure 14:
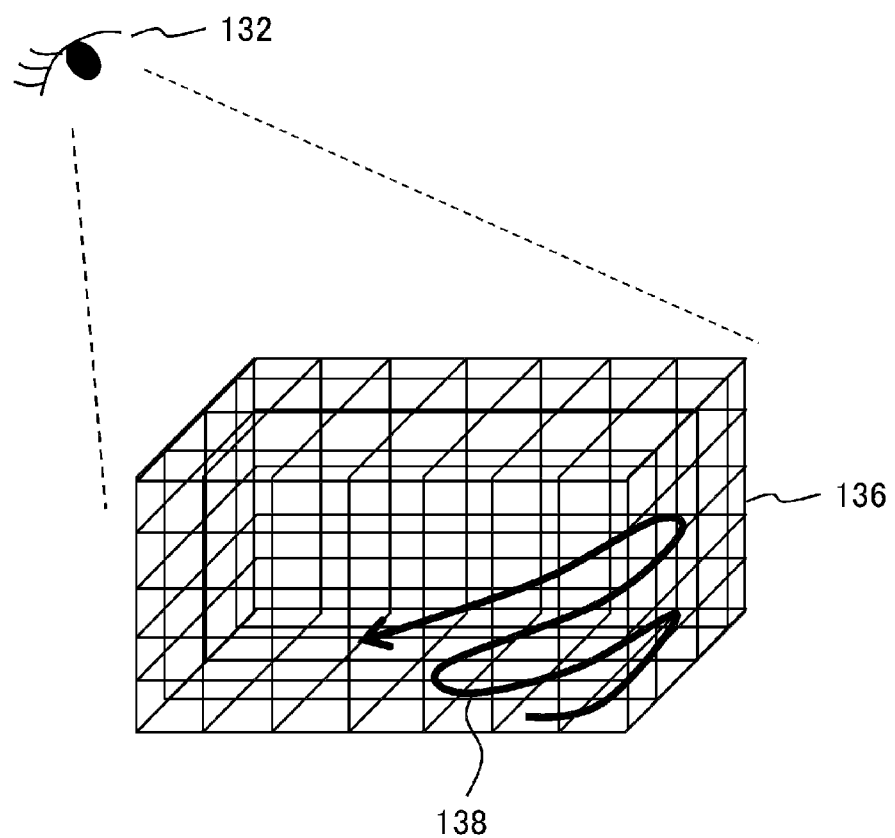
FIG. 14 is a diagram for explaining another method for drawing a three-dimensional object in the present embodiment.

FIG. 14 is a diagram for explaining another method for drawing a three-dimensional object. In the case of the figure, slice image groups for an x axis, a y axis, and a z axis are used at the same time as texture images in three directions. A commonly-practiced computer graphics drawing process can be applied to a method for drawing a three-dimensional object 136, in which a texture is attached to each surface thereof, according to the position of a viewpoint 132. On the other hand, in the case of the present embodiment, slice images in each direction has an alpha channel, and superimposition starting from a pixel away from the viewpoint 132 is thus necessary as described above.

However, when the slice images in the three directions are used at the same time, it is difficult to identify a combination of slice images in order starting from the farthest from the viewpoint. Thus, as shown in the figure, the three-dimensional object 136 is divided in a lattice shape according to the slice image groups in the three directions. In the figure, straight lines that intersect one another and that are shown in the three-dimensional object 136 represent respective edges of the slice images. When a three-dimensional array of small cuboids obtained by such division is used, the order of being away from the viewpoint 132 can be easily specified.

An arrow 138 in the figure schematically shows such order. By performing superimposition on the screen using respective pixel values of slice images that constitute a surface of each of the cuboids in the order shown by the arrow 138, the three-dimensional object 136 can be expressed while allowing for both transparent and translucent states. In the case of this mode, the slice image management unit 52 loads data of the slice image groups in the three directions regardless of the position of the viewpoint.

Figure 15:
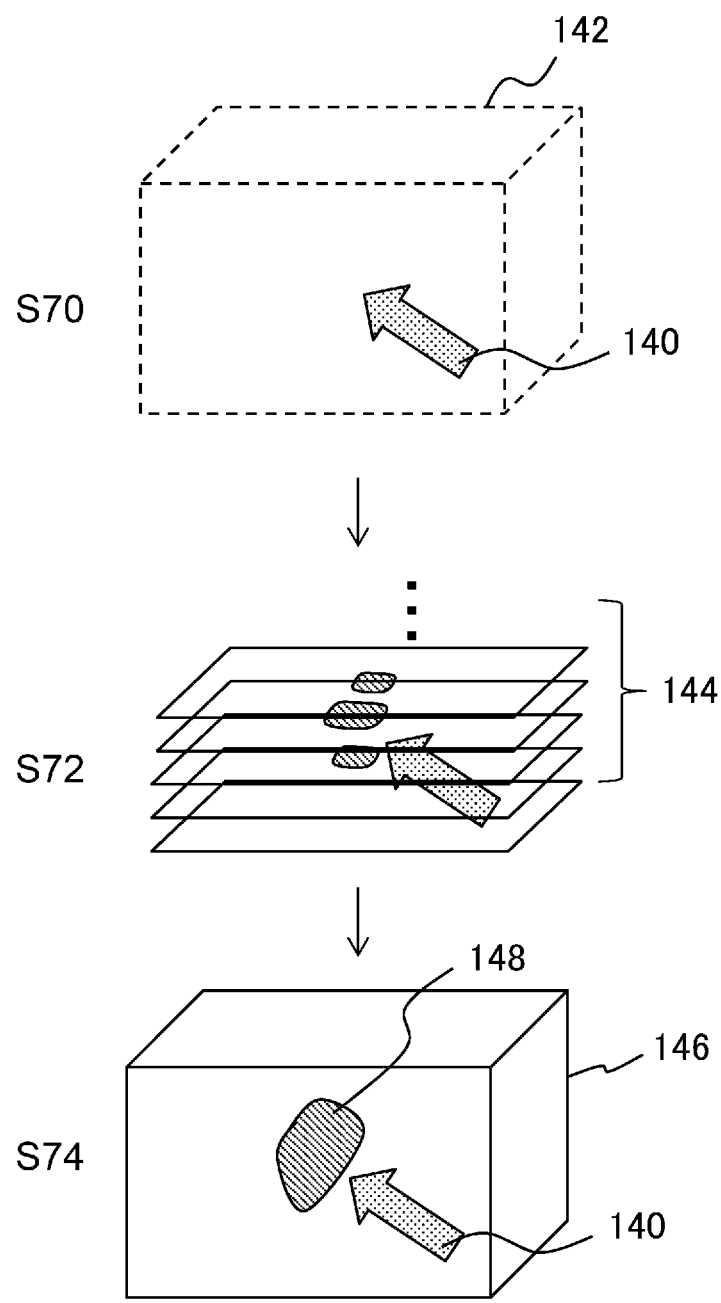
FIG. 15 is a diagram for schematically illustrating a processing procedure for drawing a three-dimensional object after drawing an additional object first in the present embodiment.

An explanation is now given regarding a method for the image drawing unit 54 to draw the additional object in S38 in FIG. 9. In order to draw the additional object in a state where the additional object seems like floating in a translucent space of the three-dimensional object, it is necessary to take into consideration the order of drawing with the alpha blending drawing of the three-dimensional object. FIG. 15 schematically illustrates, as one of the methods, a processing procedure for drawing the three-dimensional object after drawing the additional object first.

First, the image drawing unit 54 prepares a virtual cuboid 142, where the three-dimensional object will be drawn at the end, according to the position of the viewpoint, and draws an additional object 140 at a necessary position inside the cuboid 142 by a commonly-practiced method (S70). In an example shown in the figure, the additional object 140 is a cursor figure of an arrow shape. The image drawing unit 54 then draws the three-dimensional object using slice images by the method described above (S72). Drawing the additional object 140 first allows for a state where the additional object 140 remains in an area of high transmittance where the alpha value is close to zero.

Upon completing the superimposition up to a slice image that is closest to the viewpoint, a state where a cursor is floating inside the three-dimensional object 146 as the additional object 140 can be drawn (S74). For example, by positioning the cursor such that the cursor points to a target object 148 that exists inside the three-dimensional object 146, presentation or the like using display can be preferably realized. In the case where the movement of the target object with time is displayed as a moving image, the trajectory of the target object may be displayed. Also, another target object (product) may be artificially displayed at a position that can be predicted based on data that is observed. In this case, the calculation of the position of the product may be performed separately, and the user may input the position as an input value.

Figure 16:
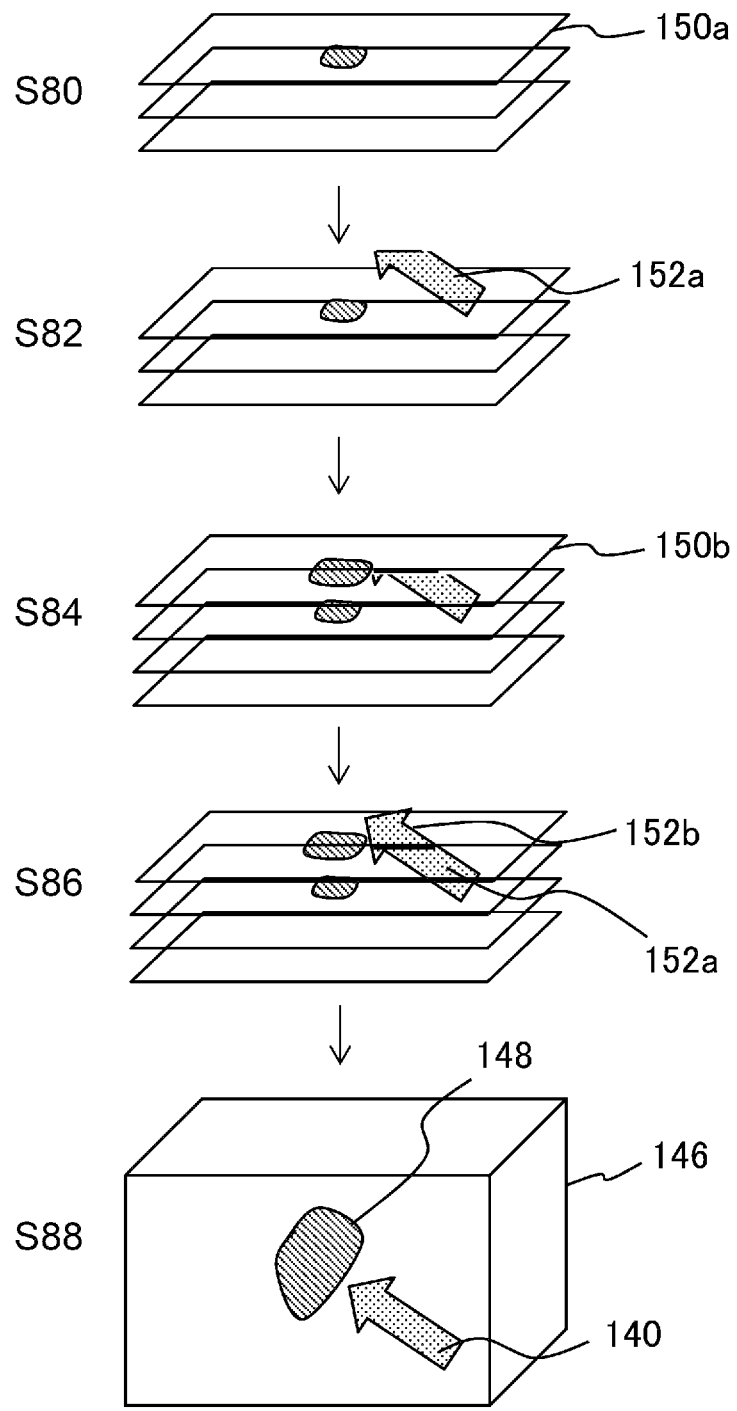
FIG. 16 is a diagram for schematically illustrating a processing procedure according to another method for drawing an additional object in the present embodiment.

FIG. 16 schematically illustrates a processing procedure according to another method for drawing the additional object. This examples shows a method of proceeding with the drawing of the three-dimensional object using slice images and drawing of the additional object in parallel with each other. First, the image drawing unit 54 performs alpha blending using the slice images up to a position where the additional object is drawn (S80). Then, the image drawing unit 54 draws a portion 152a of the additional object that should be present in a space between a slice image 150a, which is located at the uppermost position at this time, and a subsequent slice image (S82).

Then, the image drawing unit 54 superimposes a slice image 150b positioned subsequently to the slice image 150a (S84). The image drawing unit 54 then draws a portion 152b of the additional object that should be present in a space between the slice image 150b and a subsequent slice image (S86). In the case of the figure, the entire additional object has been drawn at this stage. After that, by continuing to superimpose the rest of the slice images, a state where a cursor is floating inside the three-dimensional object 146 as the additional object 140 can be drawn (S88).

Figure 17:
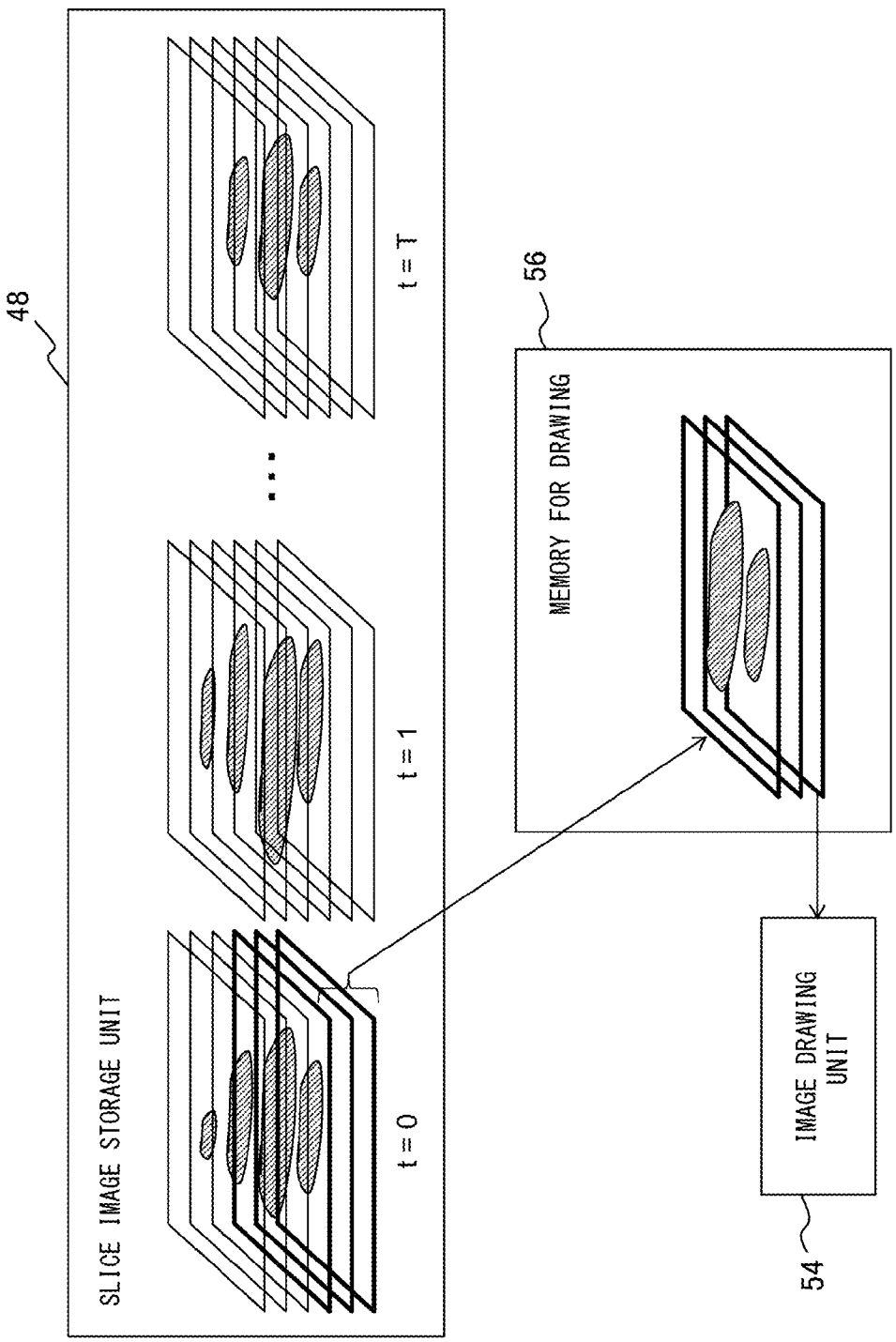
FIG. 17 is a diagram for schematically illustrating a procedure for reading slice image data when a three-dimensional object is displayed as a moving image in the present embodiment.

FIG. 17 schematically illustrates a procedure for reading slice image data when a result of measurement performed at a predetermined rate is displayed as a moving image of the three-dimensional object. In this case, a slice image group is generated for each measurement time of t=0, 1, . . . , T in the slice image storage unit 48. In practice, slice image groups in three directions are generated for each point of time. However, the illustration of such slice image groups are omitted in the figure.

Particularly when a moving image is displayed using such slice images, it is necessary to load new slice image data in response to a change in both parameters of a viewpoint and time so as to perform drawing. Thus, the processes need to become more efficient. The same applies to a case where the displayed image is not a moving image and where display is changed only by the movement of the viewpoint. When the slice image storage unit 48 is formed as a secondary storage apparatus, a process of transferring data to the memory 56 for drawing is likely to become a cause of delay in drawing.

Thus, the slice image management unit 52 performs loading into the memory 56 for drawing in order of slice images that are necessary for drawing. For example, the slice image management unit 52 specifies a slice image that is farthest from the position of the viewpoint and starts loading data starting from the data of the slice image. According to the bandwidth of a bus serving as a transfer path or the like, a load unit composed of a plurality of slice images may be formed, and the loading may be performed based on the load unit. In an example shown in the figure, the respective pieces of data of three slice images shown by thick frames are simultaneously loaded as a load unit.

Immediately after first slice image data is loaded, the image drawing unit 54 starts reading slice image data in order from the memory 56 for drawing and performs alpha blending drawing. In parallel with this drawing process, the slice image management unit 52 keeps loading respective pieces of data of subsequent slice images by a load unit by load unit basis. Upon completing the slice image group for t=0, the slice image management unit 52 loads the slice image group for t=1 in the same manner. In the present embodiment, slice images are superimposed in order so as to draw a three-dimensional object. Thus, such parallel processing is possible. As a result, responsiveness to a request for moving a viewpoint can be improved, and smooth display of a moving image can be achieved.

According to the present embodiment described above, a measurement space is expressed by a three-dimensional object by generating slice images that have alpha channels from layered image information, which is cross section information of a target object acquired in a plurality of parallel plane surfaces, and performing alpha blending drawing. This allows for visualization of the target object and surrounding states thereof in an intuitively understandable manner using a commonly-practiced image processing function without increasing processing loads or necessary resources.

Rules for determining an alpha value and color information can be variously changed at the stage of generating the slice images. Thus, the user generating an image can easily perform processing that is suitable for display contents and a purpose for display. Also, even when layered image information that is acquired first is for a single axis, slice images for a plurality of axes are generated in advance, and slice images used are switched at the time of displaying the three-dimensional object, according to the position of a viewpoint. Further, the number of the slice images is adjusted according to closeness to the viewpoint. With these features, a three-dimensional object can be displayed from every direction with no sense of incongruity even when source data represents discrete two-dimensional images. Also, slice images for a plurality of axes may be generated when they become necessary for drawing. This allows for a reduction in the capacity of memory in which the slice images are stored.

Further, a transparent space and a translucent space can be generated inside a three-dimensional object. Thus, an additional object such as a cursor can be displayed inside the three-dimensional object. As a result, indication of a target object, addition of a marker that follows the target object, and visualization of a trajectory thereof can be easily achieved, and suitable display can thus be realized in presentation or the like.

Further, when displaying a three-dimensional object, the order of slice images used according to the position of a viewpoint can be determined. Thus, a loading process and a drawing process can be performed in parallel when data is loaded into memory from a secondary storage apparatus in the order. With this, latency to the time of display can be suppressed even in a situation where the frequency of loading of data of slice images is high such as a case where a viewpoint is moved or where a three-dimensional object is shown as a moving image. As a result, smooth changing of display can be realized without increasing the capacity of memory.

Described above is an explanation of the present invention based on the embodiments. The embodiments are intended to be illustrative only, and it will be obvious to those skilled in the art that various modifications to constituting elements and processes could be developed and that such modifications are also within the scope of the present invention.

For example, a slice plane surface according to the present embodiment is a plane surface that has a predetermined angle with respect to a sensor axis or an image axis. Alternatively, the slice plane surface may be a curved surface such as a spherical surface, a curved surface with fluctuation, or the like. FIG. 18 schematically illustrates the shape of a slice image when distribution with respect to a partially cylindrical curved surface or a partially spherical surface is measured. In the figure, a sensor group 208 measures a measurement space in which a target object 216 exists. The distribution of measurement values at this time is obtained, using a z axis in a vertical direction of the figure as a sensor axis, with respect to a plurality of curved surfaces 210$a$, 210$b$, . . . , 210$n$ that are parallel to one another having the z axis as a center thereof. In the figure, these curved surfaces are shown by fan-shaped curved lines at respective cross-sectional surfaces that pass through the sensor axis.

With respect to these slice curved surfaces 210$a$, 210$b$, . . . , 210$n$, the slice image generation unit 44 generates slice images as described in the embodiment. The slice images generated at this time have the shape of a curved surface that is the same as that of the slice curved surfaces. By treating the slice images as textures, the same process can be performed regardless of whether the shape of the slice images is a plane surface or a curved surface. Also, the image axis conversion unit 50 prepares a plurality of plane surfaces or curved surfaces that cross the slice curved surfaces 210$a$, 210$b$, . . . , 210$n$ at a predetermined angle and extracts measurement values on the surfaces so as to generate slice image group in a direction different from the slice curved surfaces 210$a$, 210$b$, . . . , 210$n$.

In an example of the figure, slice image group is generated for plane surfaces 212$a$, 212$b$, . . . , 212$n$ that vertically cross the slice curved surfaces 210$a$, 210$b$, . . . , 210 and that are perpendicular to the figure. Further, slice image group arranged in the depth direction of the figure is also generated. By performing drawing using slice image groups in three directions that have been generated as described, a partially cylindrical or a partially spherical three-dimensional object can be displayed. In this case, drawing is performed for each of small solids that are divided by the slice image groups of respective directions in the order that is the same as the one shown in FIG. 14.

As described above, in the present embodiment, by treating an image as a texture regardless of the shape of a slice image, a three-dimensional object can be drawn by a commonly-practiced computer graphics technique. Therefore, regardless of a shape or intersection angle thereof, a measurement result can be similarly and easily visualized as long as the shape and the angle are known.

DESCRIPTION OF THE REFERENCE NUMERALS

10 image processing system,
12 sensor group,
14 display apparatus,
15 input apparatus,
20 image processing apparatus,
30 image data generation unit,
32 display processing unit,
42 sensor output data acquisition unit,
44 slice image generation unit,
46 vector value information storage unit,
48 slice image storage unit,
50 image axis conversion unit,
52 slice image management unit,
54 image drawing unit,
56 memory for drawing,
58 additional object image storage unit

INDUSTRIAL APPLICABILITY

As described above, the present invention is applicable to an information processing device such as computers, image processing apparatuses, and measuring apparatuses.

What is claimed is:

1. An image processing apparatus comprising:
a data acquisition unit configured to acquire distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis;
a slice image generation unit configured to generate, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and
an image drawing unit configured to display, as a virtual three-dimensional object, a three-dimensional space that is formed by arranging the slice images at respective corresponding positions on a virtual axis and performing alpha blending drawing according to a position of a viewpoint,
wherein the slice image generation unit determines an alpha value at said each position on the slice surfaces, based on at least one of the following processes:
(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or
(ii) combining at least some of the plurality of types of values to create an index, and using the index to retrieve the alpha value from a list of candidate alpha values that is set in advance.

2. The image processing apparatus according to claim 1, wherein the slice image generation unit further generates, by extracting a value at each position on a plurality of surfaces that make a predetermined angle to an axis having a direction different from that of the predetermined axis and that are located at different positions, another one of the slice image for each of the surfaces, and
wherein the image drawing unit switches, according to the position of the viewpoint, an axis of the slice image that is used.

3. The image processing apparatus according to claim 1, further comprising a slice image management unit configured to interpolate, according to a decrease in a distance between the viewpoint and the virtual three-dimensional object, a pixel value of a pixel that corresponds to the slice images that are adjacent to each other in the arrangement and interpolate between the slice images so as to generate a new slice image.

4. The image processing apparatus according to claim 1, wherein the image drawing unit displays the virtual three-dimensional object by simultaneously arranging the slice images for axes in three directions that intersect with one another at a predetermined angle and performing alpha blending drawing in order starting from the farthest from the viewpoint in units of solids divided by the surfaces of respective slice images.

5. The image processing apparatus according to claim 1, wherein the image drawing unit draws the virtual three-dimensional object by performing alpha blending drawing after drawing an additional object that has been prepared in advance at a position in a space inside the three-dimensional object, which is determined according to the position of the viewpoint.

6. The image processing apparatus according to claim 1, wherein the image drawing unit generates a drawing unit of an additional object that has been prepared in advance by dividing a model of the additional object by a surface of a slice image, draws one of slice images that sandwich a single drawing unit, and then draws the other slice image after drawing the drawing unit so as to draw the additional object inside the virtual three-dimensional object.

7. The image processing apparatus according to claim 1, wherein the image drawing unit stereoscopically displays the virtual three-dimensional object by drawing a plurality of images of the three-dimensional objects that correspond to a plurality of viewpoints having a predetermined positional relationship and then displaying the plurality of images simultaneously or sequentially.

8. The image processing apparatus according to claim 1,
wherein the data acquisition unit acquires the distribution information that corresponds to a plurality of axes,
wherein the slice image generation unit generates a slice image for each of the plurality of slice surfaces for the plurality of axes, and
wherein the image drawing unit switches, according to the position of the viewpoint, an axis of the slice image that is used.

9. An image processing method comprising:
acquiring distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis in an image processing apparatus;
generating, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and
displaying on a display apparatus, as a virtual three-dimensional object, a three-dimensional space that is formed by arranging the slice images at respective corresponding positions on a virtual axis and performing alpha blending drawing according to a position of a viewpoint,
wherein the step of generating includes determining an alpha value at said each position on the slice surfaces, based on at least one of the following processes:
(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or
(ii) combining at least some of the plurality of types of values to create an index, and using the index to retrieve the alpha value from a list of candidate alpha values that is set in advance.

10. A computer program embedded in a non-transitory computer readable recording medium, comprising:
a module configured to acquire distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis;
a module configured to generate, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and
a module configured to display on a display apparatus, as a virtual three-dimensional object, a three-dimensional space that is formed by arranging the slice images at respective corresponding positions on a virtual axis and performing alpha blending drawing according to a position of a viewpoint,
wherein the module configured to generate determines an alpha value at said each position on the slice surfaces, based on at least one of the following processes:
(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or
(ii) combining at least some of the plurality of types of values to create an index, and using the index to retrieve the alpha value from a list of candidate alpha values that is set in advance.

11. A non-transitory computer-readable recording medium having embodied thereon a computer program product comprising:
a module configured to acquire distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis;
a module configured to generate, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and
a module configured to display on a display apparatus, as a virtual three-dimensional object, a three-dimensional space that is formed by arranging the slice images at respective corresponding positions on a virtual axis and performing alpha blending drawing according to a position of a viewpoint, wherein the module configured to generate determines an alpha value at said each position on the slice surfaces, based on at least one of the following processes:

(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or (ii) combining at least some of the plurality of types of values to create an index, and using the index to retrieve the alpha value from a list of candidate alpha values that is set in advance.

12. An image processing apparatus comprising:

a data acquisition unit configured to acquire distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis;

a slice image generation unit configured to generate, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and an image drawing unit configured to display, as a virtual three-dimensional object, a three-dimensional space that is formed by arranging the slice images at respective corresponding positions on a virtual axis and performing alpha blending drawing according to a position of a viewpoint, wherein the image drawing unit displays the virtual three-dimensional object by simultaneously arranging the slice images for axes in three directions that intersect with one another at a predetermined angle and performing alpha blending drawing in order starting from a farthest position from the viewpoint in units of solids divided by the surfaces of respective slice images, wherein the slice image generation unit determines an alpha value at said each position on the slice surfaces, based on at least one of the following processes:

(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or (ii) combining at least some of the plurality of types of values to create an index, and using the index to retrieve the alpha value from a list of candidate alpha values that is set in advance.

13. An image processing apparatus comprising:

a data acquisition unit configured to acquire distribution information of a plurality of types of physical values within a three-dimensional object, the distribution information including respective two-dimensional distributions for each of a plurality of two-dimensional slice surfaces, each two-dimensional slice surface intersecting a predetermined axis through the three-dimensional object at a same angle and at different positions on the predetermined axis;

a slice image generation unit configured to generate, for each of the two-dimensional slice surfaces, a slice image that expresses the respective two-dimensional distribution as an image by determining a respective pixel value that includes an alpha value based on a set of the plurality of types of physical values at each position on a respective one of the slice surfaces; and an image drawing unit configured to display, as a virtual three-dimensional object, a three-dimensional space that is formed by arranging the slice images at respective corresponding positions on a virtual axis and performing alpha blending drawing according to a position of a viewpoint, wherein the image drawing unit draws the virtual three-dimensional object by performing alpha blending drawing after drawing an additional object that has been prepared in advance at a position in a space inside the virtual three-dimensional object, which is determined according to the position of the viewpoint, wherein the slice image generation unit determines an alpha value at said each position on the slice surfaces, based on at least one of the following processes:

(i) selecting at least one of the plurality of types of values in accordance with a predetermined criteria, comparing the at least one of the plurality of types of values at said each position on the slice surfaces with a predetermined threshold value, and determining an alpha value at said each position on the slice surfaces based on the comparison; and/or (ii) combining at least some of the plurality of types of values to create an index, and using the index to retrieve the alpha value from a list of candidate alpha values that is set in advance.

* * * * *